United States Patent
Perrow et al.

(10) Patent No.: US 8,900,277 B2
(45) Date of Patent: *Dec. 2, 2014

(54) BONE PLATE SYSTEM

(75) Inventors: Scott Perrow, Ishpeming, MI (US);
Joseph Mohar, Marquette, MI (US);
Lawrence Mosca, Marquette, MI (US);
Matthew P. Gephart, Negaunee, MI (US); Brian P. Janowski, Marquette, MI (US); Brad Fredin, Cedar Park, TX (US); Francis J. Korhonen, Negaunee, MI (US); Matthew Songer, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 340 days.

This patent is subject to a terminal disclaimer.

(21) Appl. No.: 13/069,354

(22) Filed: Mar. 22, 2011
(Under 37 CFR 1.47)

(65) Prior Publication Data
US 2012/0065690 A1    Mar. 15, 2012

Related U.S. Application Data

(63) Continuation-in-part of application No. 11/259,714, filed on Oct. 26, 2005, now Pat. No. 7,909,859, which is a continuation-in-part of application No. 10/973,891, filed on Oct. 26, 2004, now Pat. No. 7,740,649.

(60) Provisional application No. 60/548,140, filed on Feb. 26, 2004.

(51) Int. Cl.
*A61B 17/80*    (2006.01)
*A61B 17/86*    (2006.01)
*A61B 17/70*    (2006.01)

(52) U.S. Cl.
CPC .......... *A61B 17/8042* (2013.01); *A61B 17/8605* (2013.01); *A61B 17/7059* (2013.01)
USPC ............................ 606/290; 606/280; 606/289

(58) Field of Classification Search
USPC ........................................ 606/289, 290, 294
See application file for complete search history.

(56) References Cited

U.S. PATENT DOCUMENTS

| 434,503 A | 8/1890 | Corry |
| 556,642 A | 3/1893 | Reessing |

(Continued)

FOREIGN PATENT DOCUMENTS

| DE | 251246 | 12/1911 |
| DE | 2933141 | 4/1980 |

(Continued)

OTHER PUBLICATIONS

Armstrong, Gordon; Chow, Donald; The Contoured Anterior Spinal Plate, Spinal Instrumentation 1992 Williams & Wilkins Baltimore, MD, USA (5 pages).

(Continued)

*Primary Examiner* — Nicholas Woodall
(74) *Attorney, Agent, or Firm* — Fitch, Even, Tabin & Flannery LLP

(57) ABSTRACT

A bone plate system having a retainer for resisting back-out of a bone anchor from a throughbore of a bone plate is provided. In one aspect, a bone plate system having a resilient retainer disposed in a bone plate throughbore with a pair of elongate arm portions of the resilient retainer extending along opposite sides of the throughbore. In another aspect, a bone plate system having a resilient retainer with a pair of elongate interference portions completely exposed in the throughbore and spaced from each other across the throughbore to retain a head of a bone anchor received in the throughbore. In addition, a bone plate system having a resilient retainer with a pair of opposite end portions disposed within a groove of a throughbore wall such that a bone anchor may be inserted into the throughbore without contacting either of the opposite end portions of the retainer.

72 Claims, 17 Drawing Sheets

(56) References Cited

U.S. PATENT DOCUMENTS

| | | |
|---|---|---|
| 807,396 A | 12/1905 | Raveh |
| 872,897 A | 12/1907 | Chapman et al. |
| 951,680 A | 3/1910 | Center |
| 951,800 A | 3/1910 | Center |
| 1,084,680 A | 1/1914 | Wegener |
| 1,385,780 A | 7/1921 | Dodds |
| 1,409,157 A | 3/1922 | Dodds |
| 1,756,239 A | 4/1930 | Muerling |
| 1,907,506 A | 5/1933 | Coburn |
| 1,980,336 A | 11/1934 | Hoagland |
| 2,248,054 A | 7/1941 | Becker |
| 2,401,856 A | 6/1946 | Brock |
| 2,580,821 A | 1/1952 | Nicola |
| 2,780,223 A | 2/1957 | Haggland |
| 3,100,516 A | 8/1963 | Naab |
| 3,244,170 A | 4/1966 | McElvenny |
| 3,426,364 A | 2/1969 | Lumb |
| 3,534,731 A | 10/1970 | Muller |
| 3,596,656 A | 8/1971 | Kaute |
| 3,659,595 A | 5/1972 | Haboush |
| 3,695,259 A | 10/1972 | Yost |
| 3,741,205 A | 6/1973 | Markolf et al. |
| 3,842,825 A | 10/1974 | Wagner |
| RE28,841 E | 6/1976 | Allgower et al. |
| 4,003,376 A | 1/1977 | McKay et al. |
| 4,037,980 A | 7/1977 | Haentjens |
| 4,113,227 A | 9/1978 | Cigliano |
| 4,334,599 A | 6/1982 | Ritsema et al. |
| 4,388,921 A | 6/1983 | Sutter et al. |
| RE31,628 E | 7/1984 | Allgower et al. |
| 4,473,068 A | 9/1984 | Oh |
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Caspar et al. |
| 4,524,765 A | 6/1985 | de Zbikowski |
| 4,599,086 A | 7/1986 | Doty |
| 4,762,122 A | 8/1988 | Slocum |
| 4,776,330 A | 10/1988 | Chapman et al. |
| 4,794,918 A | 1/1989 | Wolter |
| 4,892,545 A | 1/1990 | Day et al. |
| 4,904,261 A | 2/1990 | Dove et al. |
| 4,943,292 A | 7/1990 | Foux |
| 4,955,908 A | 9/1990 | Frey et al. |
| 4,957,497 A | 9/1990 | Hoogland et al. |
| 4,964,403 A | 10/1990 | Karas et al. |
| 5,002,544 A | 3/1991 | Klaue et al. |
| 5,041,113 A | 8/1991 | Biedermann et al. |
| 5,041,114 A | 8/1991 | Chapman et al. |
| 5,053,036 A | 10/1991 | Perren et al. |
| 5,057,111 A | 10/1991 | Park |
| 5,085,660 A | 2/1992 | Lin |
| 5,108,395 A | 4/1992 | Laurain |
| 5,113,685 A | 5/1992 | Asher et al. |
| 5,127,912 A | 7/1992 | Ray et al. |
| 5,127,914 A | 7/1992 | Calderale et al. |
| 5,129,899 A | 7/1992 | Small et al. |
| 5,129,903 A | 7/1992 | Luhr et al. |
| 5,139,498 A | 8/1992 | Astudillo Ley |
| 5,147,360 A | 9/1992 | Dubousset |
| 5,147,361 A | 9/1992 | Ojima et al. |
| 5,151,103 A | 9/1992 | Tepic et al. |
| 5,180,381 A | 1/1993 | Aust et al. |
| 5,190,544 A | 3/1993 | Chapman et al. |
| 5,234,431 A | 8/1993 | Keller |
| 5,261,910 A | 11/1993 | Warden et al. |
| 5,269,784 A | 12/1993 | Mast |
| 5,275,601 A | 1/1994 | Goglewski et al. |
| 5,304,179 A | 4/1994 | Wagner |
| 5,324,290 A | 6/1994 | Zdeblick et al. |
| 5,326,206 A | 7/1994 | Moore |
| 5,330,535 A | 7/1994 | Moser et al. |
| 5,344,421 A | 9/1994 | Crook |
| 5,346,492 A | 9/1994 | Morgan |
| 5,364,399 A | 11/1994 | Lowery |
| 5,380,323 A | 1/1995 | Howland |
| 5,382,248 A | 1/1995 | Jacobson et al. |
| 5,397,363 A | 3/1995 | Gelbard |
| 5,397,364 A | 3/1995 | Kozak et al. |
| 5,423,826 A | 6/1995 | Coates et al. |
| 5,454,769 A | 10/1995 | Chen |
| 5,458,641 A | 10/1995 | Ramirez Jimenez |
| 5,468,242 A | 11/1995 | Reisberg |
| 5,478,342 A | 12/1995 | Kohrs |
| 5,486,176 A | 1/1996 | Hildebrand et al. |
| 5,501,684 A | 3/1996 | Schlapfer et al. |
| 5,520,690 A | 5/1996 | Errico et al. |
| 5,520,696 A | 5/1996 | Wenstrom, Jr. |
| 5,522,899 A | 6/1996 | Michelson |
| 5,527,311 A | 6/1996 | Procter et al. |
| 5,531,746 A | 7/1996 | Errico et al. |
| 5,534,027 A | 7/1996 | Hodorek |
| 5,534,032 A | 7/1996 | Hodorek |
| 5,549,612 A | 8/1996 | Yapp et al. |
| 5,569,247 A | 10/1996 | Morrison |
| 5,569,251 A | 10/1996 | Baker et al. |
| 5,571,109 A | 11/1996 | Bertagnoli |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,144 A | 4/1997 | Yapp et al. |
| 5,620,443 A | 4/1997 | Gertzbein et al. |
| 5,643,265 A | 7/1997 | Errico et al. |
| 5,647,872 A | 7/1997 | Gilbert et al. |
| 5,651,651 A | 7/1997 | Spencer |
| 5,653,708 A | 8/1997 | Howland |
| 5,667,513 A | 9/1997 | Torrie et al. |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,690,631 A | 11/1997 | Duncan et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,725,588 A | 3/1998 | Errico et al. |
| 5,735,850 A | 4/1998 | Baumgartner et al. |
| 5,735,853 A | 4/1998 | Olerud |
| 5,735,899 A | 4/1998 | Schwartz et al. |
| 5,741,258 A | 4/1998 | Klaue et al. |
| 5,766,176 A | 6/1998 | Duncan |
| 5,766,254 A | 6/1998 | Gelbard |
| 5,797,912 A | 8/1998 | Runciman et al. |
| 5,800,433 A | 9/1998 | Benzel et al. |
| 5,807,396 A | 9/1998 | Raveh |
| 5,810,823 A | 9/1998 | Klaue et al. |
| 5,814,048 A | 9/1998 | Morgan |
| 5,840,078 A | 11/1998 | Yerys |
| 5,843,082 A | 12/1998 | Yuan et al. |
| 5,876,402 A | 3/1999 | Errico et al. |
| 5,879,389 A | 3/1999 | Koshino |
| 5,888,221 A | 3/1999 | Gelbard |
| 5,904,683 A | 5/1999 | Pohndorf et al. |
| 5,951,557 A | 9/1999 | Luter |
| 5,951,558 A | 9/1999 | Fiz |
| 5,954,722 A | 9/1999 | Bono |
| 5,964,762 A | 10/1999 | Biedermann et al. |
| 5,976,141 A | 11/1999 | Haag et al. |
| 5,980,540 A | 11/1999 | Bruce |
| 5,984,924 A | 11/1999 | Asher et al. |
| 6,017,345 A | 1/2000 | Richelsoph |
| 6,022,350 A | 2/2000 | Ganem |
| 6,030,389 A | 2/2000 | Wagner et al. |
| 6,036,693 A | 3/2000 | Yuan et al. |
| 6,039,740 A | 3/2000 | Olerud |
| 6,090,111 A | 7/2000 | Nichols |
| 6,102,912 A | 8/2000 | Cazin et al. |
| 6,106,557 A | 8/2000 | Robioneck et al. |
| 6,117,173 A | 9/2000 | Taddia et al. |
| 6,129,730 A | 10/2000 | Bono et al. |
| 6,132,434 A | 10/2000 | Sherman et al. |

(56) References Cited

U.S. PATENT DOCUMENTS

| | | |
|---|---|---|
| 6,139,550 A | 10/2000 | Michelson |
| 6,152,927 A | 11/2000 | Farris et al. |
| 6,159,213 A | 12/2000 | Rogozinski |
| 6,183,476 B1 | 2/2001 | Gerhardt et al. |
| 6,189,422 B1 | 2/2001 | Stihl |
| 6,193,720 B1 | 2/2001 | Yuan et al. |
| 6,193,721 B1 | 2/2001 | Michelson |
| 6,206,881 B1 | 3/2001 | Frigg et al. |
| 6,206,882 B1 | 3/2001 | Cohen |
| 6,214,005 B1 | 4/2001 | Benzel et al. |
| 6,224,602 B1 | 5/2001 | Hayes |
| 6,228,085 B1 | 5/2001 | Theken et al. |
| 6,235,032 B1 | 5/2001 | Linkl |
| 6,235,033 B1 | 5/2001 | Brace et al. |
| 6,235,034 B1 | 5/2001 | Bray |
| 6,241,731 B1 | 6/2001 | Fiz |
| 6,254,603 B1 | 7/2001 | Gertzbein et al. |
| 6,257,593 B1 | 7/2001 | White |
| 6,258,089 B1 | 7/2001 | Campbell et al. |
| 6,261,042 B1 | 7/2001 | Pratt |
| 6,261,291 B1 | 7/2001 | Talaber et al. |
| 6,273,889 B1 | 8/2001 | Richelsoph |
| 6,290,703 B1 | 9/2001 | Ganem |
| 6,293,949 B1 | 9/2001 | Justis et al. |
| 6,306,136 B1 | 10/2001 | Baccelli |
| 6,306,139 B1 | 10/2001 | Fuentes |
| 6,322,562 B1 | 11/2001 | Wolter |
| 6,328,738 B1 | 12/2001 | Suddaby |
| 6,331,179 B1 | 12/2001 | Fried et al. |
| 6,332,887 B1 | 12/2001 | Knox |
| 6,335,034 B1 | 1/2002 | Drizen et al. |
| 6,342,055 B1 | 1/2002 | Eisermann et al. |
| 6,342,057 B1 | 1/2002 | Brace et al. |
| 6,361,537 B1 | 3/2002 | Anderson |
| 6,364,880 B1 | 4/2002 | Michelson |
| 6,379,364 B1 | 4/2002 | Brace et al. |
| 6,381,806 B1 | 5/2002 | Stanesic et al. |
| 6,383,186 B1 | 5/2002 | Michelson |
| 6,391,030 B1 | 5/2002 | Wagner et al. |
| 6,398,783 B1 | 6/2002 | Michelson |
| 6,402,755 B1 | 6/2002 | Pisharodi |
| 6,402,756 B1 | 6/2002 | Ralph et al. |
| 6,402,759 B1 | 6/2002 | Strong et al. |
| 6,406,478 B1 | 6/2002 | Kuo |
| 6,413,259 B1 | 7/2002 | Lyons et al. |
| 6,416,528 B1 | 7/2002 | Michelson |
| 6,423,068 B1 | 7/2002 | Reisberg et al. |
| 6,428,542 B1 | 8/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,471,704 B2 | 10/2002 | Gertzbein et al. |
| 6,478,797 B1 | 11/2002 | Paul |
| 6,503,250 B2 | 1/2003 | Paul |
| 6,527,776 B1 | 3/2003 | Michelson |
| 6,533,786 B1 | 3/2003 | Needham et al. |
| 6,537,319 B2 | 3/2003 | Whelan |
| 6,572,619 B2 | 6/2003 | Santilli |
| 6,575,975 B2 | 6/2003 | Brace et al. |
| 6,579,290 B1 | 6/2003 | Hardcastle et al. |
| 6,585,769 B1 | 7/2003 | Muhanna et al. |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,652,525 B1 | 11/2003 | Assaker et al. |
| 6,669,700 B1 | 12/2003 | Farris et al. |
| 6,692,503 B2 | 2/2004 | Foley et al. |
| 6,695,846 B2 | 2/2004 | Richelsoph et al. |
| 6,755,833 B1 | 6/2004 | Paul et al. |
| 6,890,334 B2 | 5/2005 | Brace et al. |
| 6,890,335 B2 | 5/2005 | Garbowski et al. |
| 7,001,387 B2 | 2/2006 | Farris et al. |
| 7,008,426 B2 | 3/2006 | Paul |
| 7,025,761 B2 | 4/2006 | Wang et al. |
| 7,025,769 B1 | 4/2006 | Ferree |
| 7,048,739 B2 | 5/2006 | Konieczynski et al. |
| 7,070,599 B2 | 7/2006 | Paul |
| 7,077,843 B2 | 7/2006 | Thramann et al. |
| 7,204,837 B2 | 4/2007 | Paul |
| 7,273,481 B2 | 9/2007 | Lombardo et al. |
| 7,452,370 B2 | 11/2008 | Anderson |
| 7,481,811 B2 | 1/2009 | Suh |
| 7,524,325 B2* | 4/2009 | Khalili ..................... 606/290 |
| 7,740,649 B2 | 6/2010 | Mosca et al. |
| 7,785,327 B1* | 8/2010 | Navarro et al. .............. 606/71 |
| 7,909,859 B2 | 3/2011 | Mosca et al. |
| 8,066,751 B2* | 11/2011 | Podgorski et al. ........... 606/290 |
| 8,496,693 B2 | 7/2013 | Robinson |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0016595 A1 | 2/2002 | Michelson |
| 2002/0022843 A1 | 2/2002 | Michelson |
| 2002/0045896 A1 | 4/2002 | Michelson |
| 2002/0045898 A1 | 4/2002 | Freid et al. |
| 2002/0045899 A1 | 4/2002 | Errico et al. |
| 2002/0049444 A1 | 4/2002 | Knox |
| 2002/0058939 A1 | 5/2002 | Wagner et al. |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph et al. |
| 2002/0120268 A1 | 8/2002 | Berger |
| 2002/0120271 A1 | 8/2002 | Dixon et al. |
| 2002/0120272 A1 | 8/2002 | Yuan et al. |
| 2002/0120273 A1 | 8/2002 | Needham et al. |
| 2002/0128654 A1 | 9/2002 | Steger et al. |
| 2002/0128655 A1 | 9/2002 | Michelson |
| 2002/0151893 A1 | 10/2002 | Santilli |
| 2002/0151899 A1 | 10/2002 | Bailey et al. |
| 2002/0151900 A1 | 10/2002 | Glascott |
| 2002/0156474 A1 | 10/2002 | Wack et al. |
| 2002/0161370 A1 | 10/2002 | Frigg et al. |
| 2002/0173790 A1 | 11/2002 | Chang et al. |
| 2002/0183747 A1 | 12/2002 | Jao et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023242 A1 | 1/2003 | Harrington, Jr. |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0078583 A1 | 4/2003 | Biedermann et al. |
| 2003/0093082 A1 | 5/2003 | Campbell et al. |
| 2003/0105462 A1 | 6/2003 | Haider |
| 2003/0130661 A1 | 7/2003 | Soman |
| 2003/0149434 A1 | 8/2003 | Paul |
| 2003/0153920 A1 | 8/2003 | Ralph et al. |
| 2003/0181912 A1 | 9/2003 | Michelson |
| 2003/0187440 A1 | 10/2003 | Richelsoph et al. |
| 2003/0187441 A1 | 10/2003 | Bolger et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0225409 A1 | 12/2003 | Freid et al. |
| 2004/0030338 A1 | 2/2004 | Paul |

(56) References Cited

U.S. PATENT DOCUMENTS

| | | |
|---|---|---|
| 2004/0087951 A1 | 5/2004 | Khalili |
| 2004/0097934 A1 | 5/2004 | Farris et al. |
| 2004/0097935 A1 | 5/2004 | Richelsoph et al. |
| 2004/0097950 A1 | 5/2004 | Foley et al. |
| 2004/0122426 A1 | 6/2004 | Michelson |
| 2004/0127896 A1 | 7/2004 | Lombardo et al. |
| 2004/0127899 A1 | 7/2004 | Konieczynski et al. |
| 2004/0127900 A1 | 7/2004 | Konieczynski et al. |
| 2004/0153069 A1 | 8/2004 | Paul |
| 2004/0186482 A1 | 9/2004 | Kolb et al. |
| 2004/0204710 A1 | 10/2004 | Patel et al. |
| 2004/0204716 A1 | 10/2004 | Fanger et al. |
| 2004/0204717 A1 | 10/2004 | Fanger et al. |
| 2004/0220571 A1 | 11/2004 | Assaker et al. |
| 2004/0236334 A1 | 11/2004 | Michelson |
| 2005/0038436 A1 | 2/2005 | Michelson |
| 2005/0049593 A1 | 3/2005 | Duong et al. |
| 2005/0192577 A1* | 9/2005 | Mosca et al. .................. 606/69 |
| 2005/0283152 A1 | 12/2005 | Lindemann et al. |
| 2006/0122602 A1 | 6/2006 | Konieczynski et al. |
| 2006/0122604 A1 | 6/2006 | Gorhan et al. |
| 2006/0142768 A1 | 6/2006 | Paul |
| 2006/0149256 A1 | 7/2006 | Wagner et al. |
| 2006/0200147 A1 | 9/2006 | Ensign et al. |
| 2006/0217725 A1 | 9/2006 | Suh |
| 2006/0229620 A1 | 10/2006 | Rothman et al. |
| 2006/0241616 A1 | 10/2006 | Konieczynski et al. |
| 2009/0171397 A1 | 7/2009 | Rothman et al. |
| 2009/0187218 A1 | 7/2009 | Schaffhausen |

FOREIGN PATENT DOCUMENTS

| | | |
|---|---|---|
| DE | 4409833 | 10/1995 |
| EP | 179695 | 4/1986 |
| EP | 201024 | 11/1986 |
| EP | 242842 | 10/1987 |
| EP | 251583 | 1/1988 |
| EP | 410309 | 1/1991 |
| EP | 455255 | 11/1991 |
| EP | 471418 | 2/1992 |
| EP | 502815 | 9/1992 |
| EP | 599640 | 6/1994 |
| EP | 683646 | 11/1995 |
| EP | 699057 | 3/1996 |
| EP | 767631 | 4/1997 |
| EP | 809971 | 12/1997 |
| EP | 809972 | 12/1997 |
| EP | 828459 | 3/1998 |
| EP | 874595 | 11/1998 |
| EP | 876128 | 11/1998 |
| EP | 897697 | 2/1999 |
| EP | 903113 | 3/1999 |
| EP | 984728 | 3/2000 |
| EP | 988833 | 3/2000 |
| EP | 995404 | 4/2000 |
| EP | 999796 | 5/2000 |
| EP | 1106144 | 6/2001 |
| EP | 1169971 | 1/2002 |
| EP | 1185210 | 3/2002 |
| EP | 1220645 | 7/2002 |
| EP | 1285632 | 2/2003 |
| EP | 1306058 | 5/2003 |
| EP | 1336383 | 8/2003 |
| EP | 1340468 | 9/2003 |
| EP | 1346697 | 9/2003 |
| EP | 1364623 | 11/2003 |
| FR | 994718 | 11/1951 |
| FR | 2435243 | 4/1980 |
| FR | 2519857 | 7/1983 |
| FR | 2556583 | 6/1985 |
| FR | 2740321 | 4/1997 |
| FR | 2794963 | 12/2000 |
| FR | 2810532 | 12/2001 |
| SU | 1424824 | 9/1988 |
| WO | 88/03781 | 6/1988 |
| WO | 91/03994 | 4/1991 |
| WO | 94/17744 | 8/1994 |
| WO | 95/25474 | 9/1995 |
| WO | 95/31941 | 11/1995 |
| WO | 96/00530 | 1/1996 |
| WO | 96/05778 | 2/1996 |
| WO | 96/08206 | 3/1996 |
| WO | 96/29948 | 10/1996 |
| WO | 96/39975 | 12/1996 |
| WO | 97/22306 | 6/1997 |
| WO | 98/34553 | 8/1998 |
| WO | 98/34556 | 8/1998 |
| WO | 98/51226 | 11/1998 |
| WO | 99/04718 | 2/1999 |
| WO | 99/21502 | 5/1999 |
| WO | 99/56653 | 11/1999 |
| WO | 00/03653 | 1/2000 |
| WO | 00/25689 | 5/2000 |
| WO | 00/66011 | 11/2000 |
| WO | 00/78238 | 12/2000 |
| WO | 01/01874 | 1/2001 |
| WO | 01/26566 | 4/2001 |
| WO | 01/26567 | 4/2001 |
| WO | 01/49191 | 7/2001 |
| WO | 01/64144 | 9/2001 |
| WO | 01/82804 | 11/2001 |
| WO | 01/82805 | 11/2001 |
| WO | 01/89400 | 11/2001 |
| WO | 01/89428 | 11/2001 |
| WO | 02/076317 | 10/2002 |
| WO | 02/080789 | 10/2002 |
| WO | 02/098276 | 12/2002 |
| WO | 02/098277 | 12/2002 |
| WO | 03/007826 | 1/2003 |
| WO | 03/017856 | 3/2003 |
| WO | 03/053262 | 7/2003 |
| WO | 03/063714 | 8/2003 |
| WO | 03/071966 | 9/2003 |
| WO | 2006/047581 | 5/2006 |
| WO | 2006/055156 | 5/2006 |
| WO | 2009052318 A2 | 4/2009 |

OTHER PUBLICATIONS

Benzel, Edward, MD; Leon, Steven, MD, Enhancing Cervical Spine Fusion, www.medscape.com, Mar. 2001, (31 pages).

Bose, Bikash, MD. Anterior Cervical Fusion Using Caspar Plating: Analysis of Results and Review of the Literature, Surgical Neurology, vol. 29, No. 1, Jan. 1998, Elsevier Biomedical, New York, NY, USA (8 pages).

Caspar W; Barbier DD; Klara PM; Abstract: Anterior cervical fusion and Caspar plate stabilization for cervical trauma, Neurosurgery, Oct. 25, 1989 (4):491-502 (1 page).

Chang, J.H., Chang, G.L., Hsu, A.T. Kinematic Study of Cervical Vertebrae Adjacent to Fixation Procedures, Institute of Biomedical Engineering, Natl Cheng Kung University, Taiwan, R.O.C. (2 pages).

Chen, Ing-Ho; Yang, Rong-Sen; Chen, Po-Quang, Plate Fixation for Anterior Cervical Interbody Fusion, Journal of the Formosan Medical Association, vol. 90, No. 2, Feb. 1991, Scientific Communications International; Hong Kong, China (4 pages).

Clausen, John D.,B.S; Ryken, Timothy C., MD; Traynelis, Vincent C., MD; Sawin, Paul D., MD; Dexter, Franklin, MD, Ph.D.; Goel, Vijay K., Ph.D. Biomechanical Evaluation of Caspar and Cervical Spine Locking Plate Systems in a Cadaeric Model. J. Neurosurgy, vol. 84, Jun. 1996, 1039-1045 (9 pages).

International Preliminary Report on Patentability dated May 1, 2007, from the International Bureau in corresponding International (PCT) Application No. PCT/US2005/038537 (4 pages).

International Search Report dated Jul. 18, 2006, from the International Searching Authority in corresponding International (PCT) Application No. PCT/US2005/38537 (3 pages).

Moftakhar, Roham, MD; Trost, Gregory, MD;p Anterior Cervical Plates: A Historical Perspective, Neurosurgical Focus, vol. 16, No. 1, Jan. 2004, Charlottesville, VA, USA, (5 pages).

Omeis, Ibrahim, MD; Demattia, Joseph, MD; Hillard, Virany, MD; Murali, Raj, MD; Das, Kaushik, MD, History of Instrumentation for

(56) References Cited

OTHER PUBLICATIONS

Stabilization of the Subaxial Cervical Spine, Neurosurgical Focus, vol. 16, No. 1, Jan. 2004, Charlottesville, VA, USA (6 pages).

Paramore, Christopher G., MD; Dickman, Curtis A., MD; Sonntag, Volker K.H., MD; Radiographic and Clinical Follow-up Review of Caspar Plates in 49 Patients, J. Neurosurgy, vol. 84, Jun. 1996, 957-961 (5 pages).

Pitzen, T.; Steudel, W.I.; Oxland, T; Abstract: The effect of posterior element injury on cervical spine flexibility while using anterior plates with and without posterior fixation, an in vitro trauma model, Neurochirurgische Klinik, Universitatskliniken des Saarlanders, Homburg; Division of Orthopedic Engineering Research, University of British Columbia, Vancouver, Canada (1 page).

Takahashi, Toshiyuki; Tominaga, Teija; Yoshimoto, Takashi et al.; Biomechanical evaluation of hydroxyapatite intervertebral graft and anterior cervical plating in a porcine cadaveric model, Bio-Medical Materials and Engineering 7 (1997) 121-127 (7 pages).

Tippets, Richard H., MD; Apfelbaum, Ronald I., MD; Anterior Cervical Fusion with the Caspar Instrumentation System, Neurosurgery, vol. 22, No. 6, Part 1, Jun. 1998 (6 pages).

Zdeblic, Thomas A., MD; Ghanayem, Alexander, J. MD; Rapoff, Andrew J., MS; Swain, Carol, MS; Bassett, Tim, MD; Cooke, Mary E., MS; Markel, Mark DVM; Cervical Interbody Fusion Cages; An Animal Model With and Without Bone Morphogenetic Protein, SPINE 1998 vol. 23, No. 7, pp. 758-766 (8 pages).

Written Opinion dated Jul. 18, 2006, from the International Searching Authority in corresponding International (PCT) Application No. PCT/US2005/038537 (3 pages).

United States Patent and Trademark Office, Non-Final Office Action mailed May 22, 2007, in related U.S. Appl. No. 10/973,891 (15 pages).

Amendment, filed Nov. 20, 2007, in related U.S. Appl. No. 10/973,891 (18 pages).

United States Patent and Trademark Office, Final Office Action mailed Mar. 3, 2008, in related U.S. Appl. No. 10/973,891 (13 pages).

Response to Notice of Non-Compliant Amendment and First Substitute Amendment, filed Oct. 6, 2008, in related U.S. Appl. No. 10/973,891 (18 pages).

United States Patent and Trademark Office, Election Requirement mailed Jan. 26, 2009, in related U.S. Appl. No. 10/973,891 (5 pages).

Response to Election Requirement, filed Feb. 24, 2009, in related U.S. Appl. No. 10/973,891 (2 pages).

United States Patent and Trademark Office, Non-Final Office Action mailed May 13, 2009, in related U.S. Appl. No. 10/973,891 (6 pages).

Amendment, filed Sep. 14, 2009, in related U.S. Appl. No. 10/973,891 (12 pages).

United States Patent and Trademark Office, Election Requirement mailed May 11, 2009, in related U.S. Appl. No. 11/259,714 (9 pages).

Response to Election Requirement, filed Jul. 6, 2009, in related U.S. Appl. No. 11/259,714 (2 pages).

United States Patent and Trademark Office, Non-Final Office Action mailed Oct. 27, 2009, in related U.S. Appl. No. 11/259,714 (7 pages).

Amendment, filed Apr. 27, 2010, in related U.S. Appl. No. 11/259,714 (21 pages).

United States Patent and Trademark Office, Final Office Action mailed Jul. 7, 2010, in related U.S. Appl. No. 11/259,714 (7 pages).

Amendment After Final, filed Oct. 7, 2010, in related U.S. Appl. No. 11/259,714 (12 pages).

United States Patent and Trademark Office, Notice of Allowance and Fees due, mailed Jan. 20, 2010, in related U.S. Appl. No. 10/973,891 (8 pages).

United States Patent and Trademark Office, Notice of Allowance and Fees due, mailed Oct. 13, 2010, in related U.S. Appl. No. 11/259,714 (4 pages).

\* cited by examiner

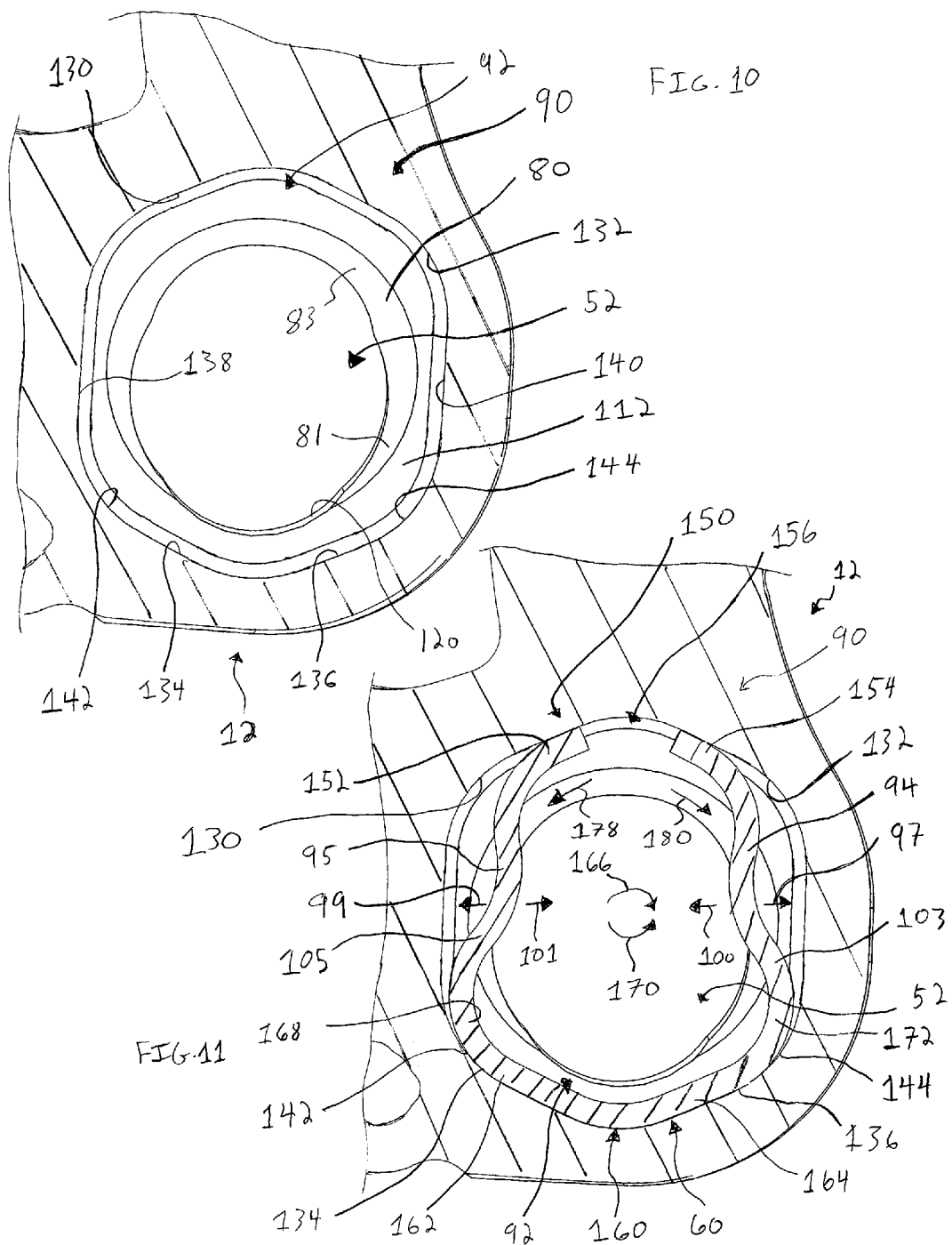

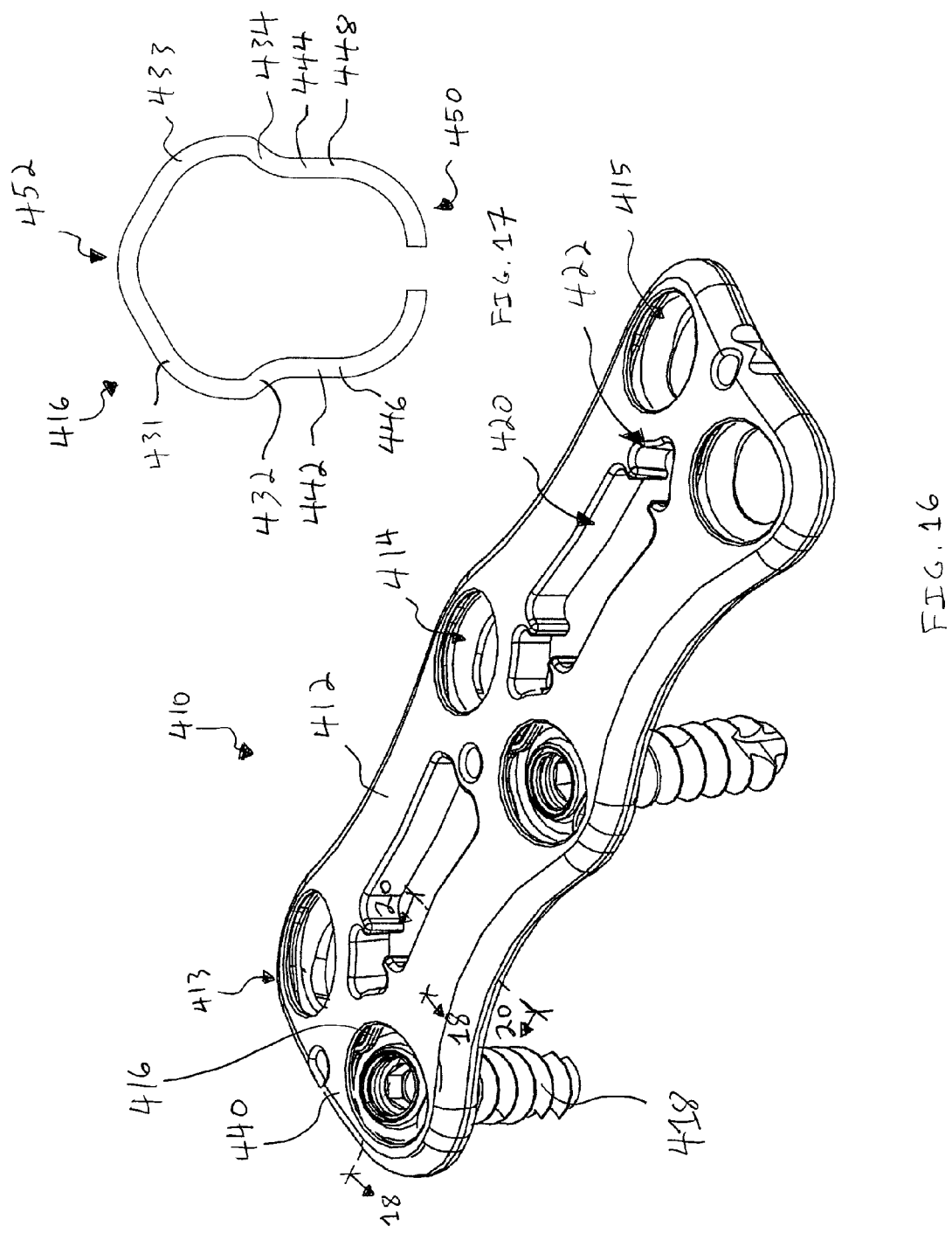

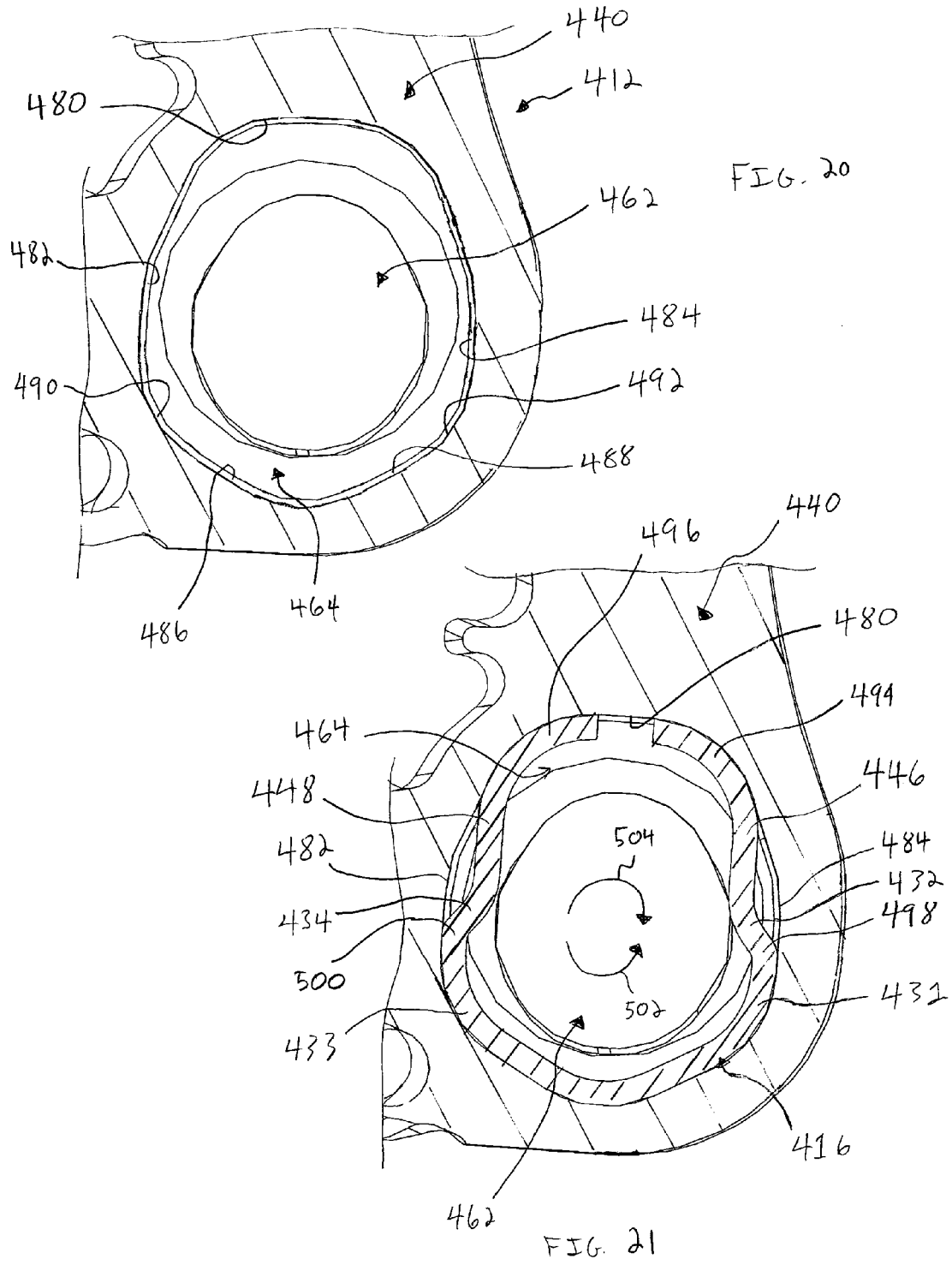

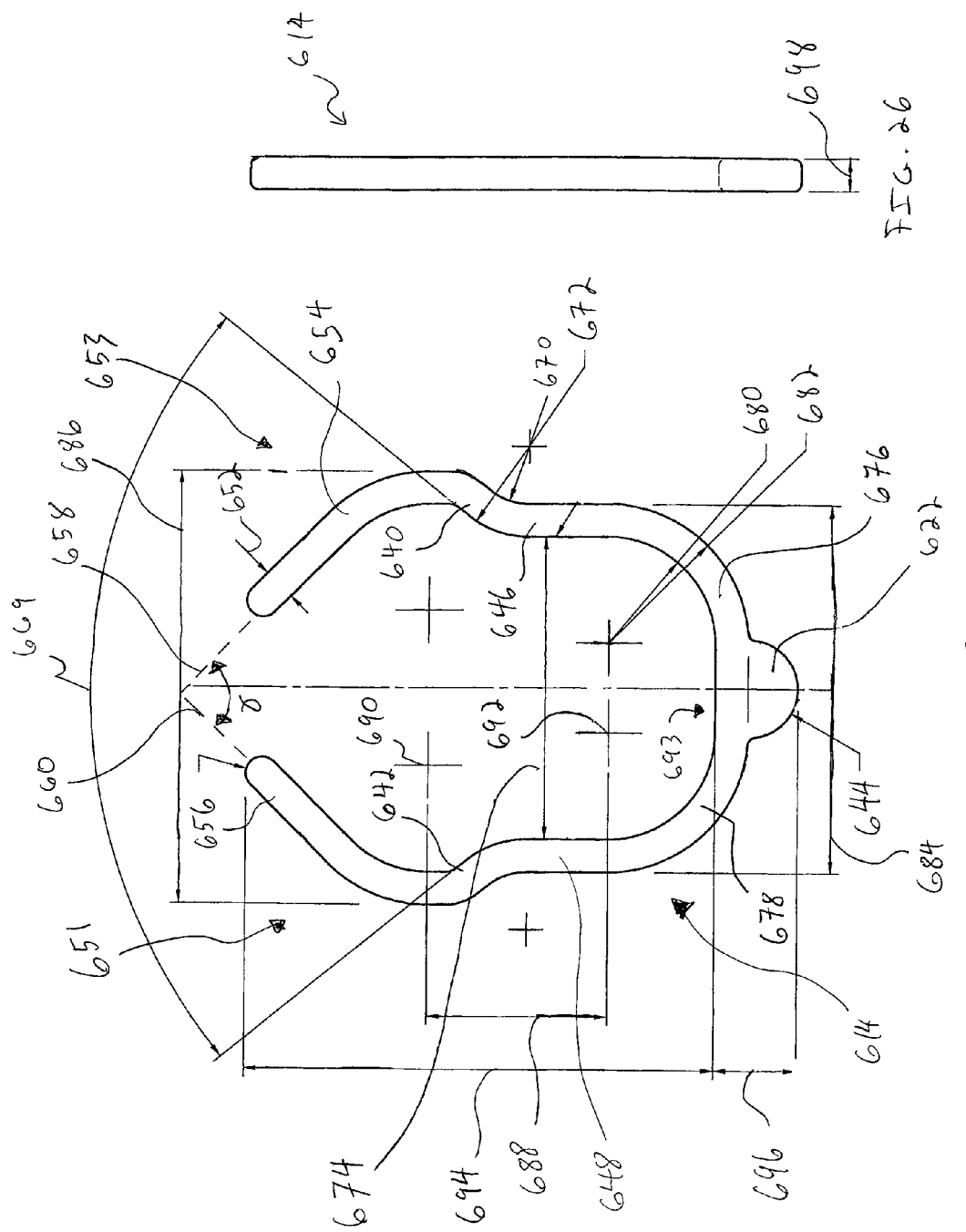

BONE PLATE SYSTEM

CROSS-REFERENCE TO RELATED APPLICATIONS

This application is a continuation-in-part of U.S. patent application Ser. No. 11/259,714, filed Oct. 26, 2005, and issued as U.S. Pat. No. 7,909,859 on Mar. 22, 2011, "Bone Plate System and Methods," which is a continuation-in-part of U.S. patent application Ser. No. 10/973,891, filed Oct. 26, 2004 and issued as U.S. Pat. No. 7,740,649 on Jun. 22, 2010, titled "Bone Plate System and Methods," which claims the benefit of U.S. Provisional Patent Application No. 60/548,140, filed Feb. 26, 2004, titled "Bone Plate System," the entirety of which are all hereby incorporated by reference.

FIELD OF THE INVENTION

The invention relates to bone plate systems and, more particularly, to bone plate systems having retention systems that resist bone anchor back out from throughbores of the bone plate.

BACKGROUND OF THE INVENTION

There are presently many different types of bone plate systems for securing bones, bone fragments, and/or implants in relative position so that the bones or bone fragments may fuse or heal. A shortcoming of some bone plates is the backing out or loosening of bone anchors that secure the bone plate to one or more bones. If the bone anchors loosen, the bones may not be properly secured and may move relative to each other. This may compromise the ability to achieve optimal bone fusion and bone alignment, may lead to loss of graft material, and may cause damage or loss of bone. When the bone plate is a dynamic or dynamized bone plate, such that at least some screws may move relative to the bone plate, these issues may be further compounded or exacerbated by a screw backing out.

One approach to limiting back-out of a bone anchor from a bone plate is disclosed in U.S. Pat. No. 6,599,290 to Bailey et al., which utilizes a locking ring positioned within a throughbore. The bone anchor has a head with a tapered lower segment that resiliently expands the locking ring as the bone anchor head passes through a central opening of the locking ring and into the throughbore. The locking ring resiliently retracts over the top of the bone anchor once the head is seated within the throughbore and resists back-out of the bone anchor from the throughbore. The locking ring, however, has a flange extending above the upper surface of the bone plate that may contact and irritate adjacent tissues.

United States Patent Application Publication No. 2005/0049593 to Duong et al. discloses another approach to limiting back-out of a bone anchor from a throughbore. Specifically, Duong et al. disclose an omega-shaped resilient clip that snaps into a perimetral groove on a head of the bone anchor to resist back-out of the bone anchor from the throughbore. The bone anchor head includes upper and lower radially enlarged sections that define the perimetral groove therebetween. The bone plate is relatively thick to permit both of the radially enlarged sections of the bone anchor head to be received within the throughbore. Further, the upper radially enlarged section of the bone anchor head interferes with arms of the resilient clip and limits pivoting of the bone anchor when the clip is engaged with the perimetral groove on the bone anchor head.

SUMMARY OF THE INVENTION

In one form of the invention, a bone plate system is provided having a resilient retainer disposed in a bone plate throughbore to resist back-out of a bone anchor from the throughbore. The throughbore has a predetermined axial length along a bone plate longitudinal axis and a pair of opposite axial end portions along the axial length of the throughbore. The resilient retainer has a pair of elongate arm portions extending along opposite sides of the throughbore and interference portions of the elongate arm portions disposed in the throughbore to be adjacent or in a predetermined one of the axial end portions of the throughbore. The resilient retainer also has bone plate engaging portions at the other axial end portion of the throughbore. The other axial end portion of the throughbore and an enlarged head of the bone anchor are configured and sized relative to each other to allow the bone anchor to extend obliquely in the throughbore with a raised portion of the bone anchor head generally level with the retainer bone plate engaging portions at the other axial end portion of the throughbore and a lowered portion of the bone anchor head disposed below the retainer interference portions in the throughbore. In this manner, the thickness of the bone plate may be reduced as the entirety of enlarged head of the bone anchor need not be disposed below the interference portions of the resilient retainer when the bone anchor extends obliquely in the bore. In one embodiment, the throughbore has a seat with a wide portion disposed below the interference portions and a narrow portion axially offset from the interference portions in the throughbore. The seat includes a wall extending below the narrow portion of the seat for engaging a shank of the bone anchor and limiting the bone anchor to a predetermined maximum oblique angle relative to a central bore axis. With the enlarged head of the bone anchor received in the bore and the bone anchor extending at the maximum oblique angle, the narrow portion of the throughbore seat positions the raised portion of the enlarged head at a predetermined height within the throughbore where the raised portion of the head remains below a top surface of the bone plate. In this manner, the raised portion of the enlarged head avoids interfering with adjacent tissues even when the bone anchor is extending at the maximum oblique angle in the bore. Further, the thickness of the bone plate may be minimized for a given bone anchor and desired maximum oblique insertion angle without compromising or reducing back-out resistance provided by the interference portions of the resilient retainer.

In another form of the invention, a bone plate system is provided having a bone plate with a plurality of throughbores and bore walls extending about the throughbores. The bone plate system has a resilient retainer received in each of the throughbores to resist back-out of bone anchors from the throughbores. Each resilient retainer has a pair of elongate interference portions disposed in an associated throughbore that extend along either side of the throughbore spaced from the bore wall thereof to be completely exposed in the throughbore and spaced from each other across the throughbore to retain a head portion of a bone anchor received in the throughbore. In this manner, the interference portions of the resilient retainers can shift to a deflected position in the associated throughbore as a bone anchor is driven into the throughbore and resiliently shift back to an interference position above the bone anchor head portion once the head portion is seated in the throughbore. Further, the spacing between the interference portions and the bore wall provides clearance for the interference portions to deflect out of the way of the bone anchor as the bone anchor is inserted into the throughbore. In one embodiment, the resilient retainers include bone plate engaging portions configured for being held in the bone plate and transition portions extending between the bone plate engaging portions and the interference portions. The transition portions extend along opposite sides of a raised portion of an associated bone anchor head portion when the head portion is received in the throughbore and the bone anchor extends obliquely to a central axis of the throughbore. Because the transition portions of the resilient retainer are positioned out of the way of the raised portion, the interference portions may resiliently shift back to the interference position above the head portion without contact between the transition portions and the raised portion of the bone anchor head portion restricting movement of the interference portions.

In one aspect of the invention, a bone plate system is provided having a resilient retainer disposed within a throughbore to resist bone anchor back-out therefrom. The retainer has a pair of interference portions that are spaced from each other and extend along either side of the throughbore to be in interference with a head portion of the bone anchor. The bone plate has a bore wall extending about the throughbore and a groove in the bore wall which opens to the throughbore. The resilient retainer has a pair of opposite end portions disposed at opposite ends of the throughbore with the opposite end portions of the retainer disposed in the groove. In this manner, the bone anchor may be inserted into the throughbore without the bone anchor interfering or snagging on the end portions of the resilient retainer since the end portions are received in the groove radially recessed in the bore wall. In one embodiment, the resilient retainer includes transition portions disposed between the interference portions and one of the end portions of the retainer. The transition portions are spaced from the one end portion to permit a raised portion of the seated bone anchor head portion to extend between the transition portions and the one end portion of the retainer when the bone anchor head portion is received in the throughbore and the bone anchor extends obliquely in the throughbore. In this manner, the transition portions and the one end portion of the retainer generally extend around the raised portion of the seated bone anchor head portion such that the transition portions and the one end portion are out of the way of the raised portion and avoid restricting the bone anchor from extending at oblique angles within the throughbore. Further, the interference portions are free to resiliently shift back to an interference position above the seated head portion to resist back-out of the bone anchor without contact between the transition portions and/or the one end portion inhibiting movement of the interference portions.

BRIEF DESCRIPTION OF THE DRAWINGS

FIG. 10 is a cross-sectional view of the bone plate system of FIG. 1 taken along line 10-10 in FIG. 1 showing one of the throughbores with the associated retainer and bone anchor removed;

FIG. 11 is a cross-sectional view of the bone plate system of FIG. 1 similar to FIG. 10 showing the retainer positioned within the throughbore;

FIG. 16 is a perspective view of a bone plate system in accordance with another form of the present invention having several bone anchors and associated retainers removed from the bone plate;

FIG. 17 is a plan view of a retainer of the bone plate system of FIG. 16;

FIG. 20 is a cross-sectional view of the bone plate system of FIG. 16 taken along line 20-20 in FIG. 16 showing a throughbore with the associated retainer and bone anchor removed;

FIG. 21 is a cross-sectional view of the bone plate system of FIG. 16 similar to FIG. 20 showing the retainer positioned within the throughbore;

FIG. 25 is a plan view of a retainer of the bone plate system of FIG. 22; and

FIG. 26 is a side elevational view of a retainer of the bone plate system of FIG. 22.

DETAILED DESCRIPTION OF THE PREFERRED EMBODIMENTS

Figure 1:
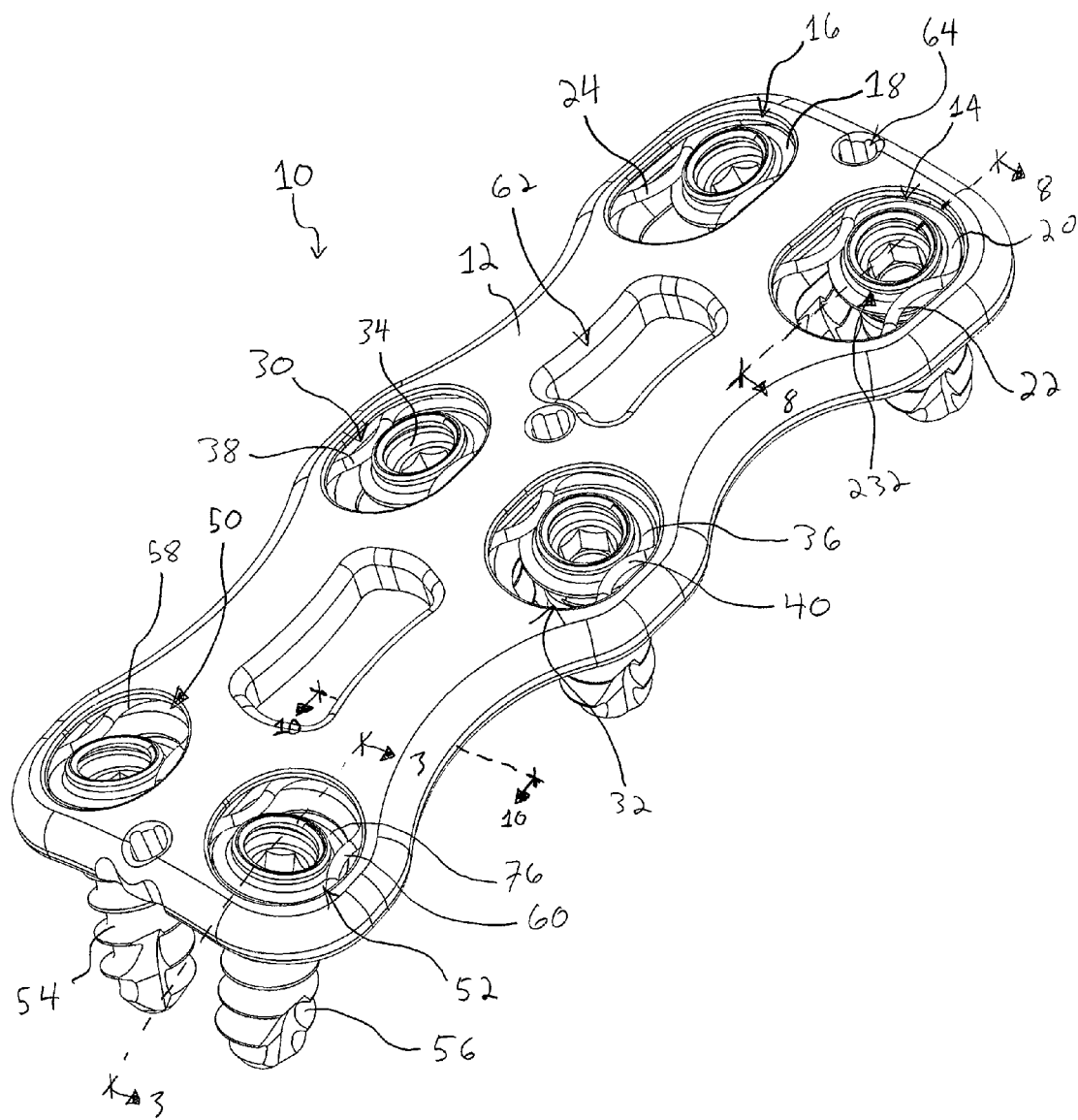
FIG. 1 is a perspective view of a bone plate system in accordance with one form of the present invention showing a bone plate including a plurality of throughbores and resilient retainers for resisting back-out of bone anchors from the throughbores.
Figure 2:
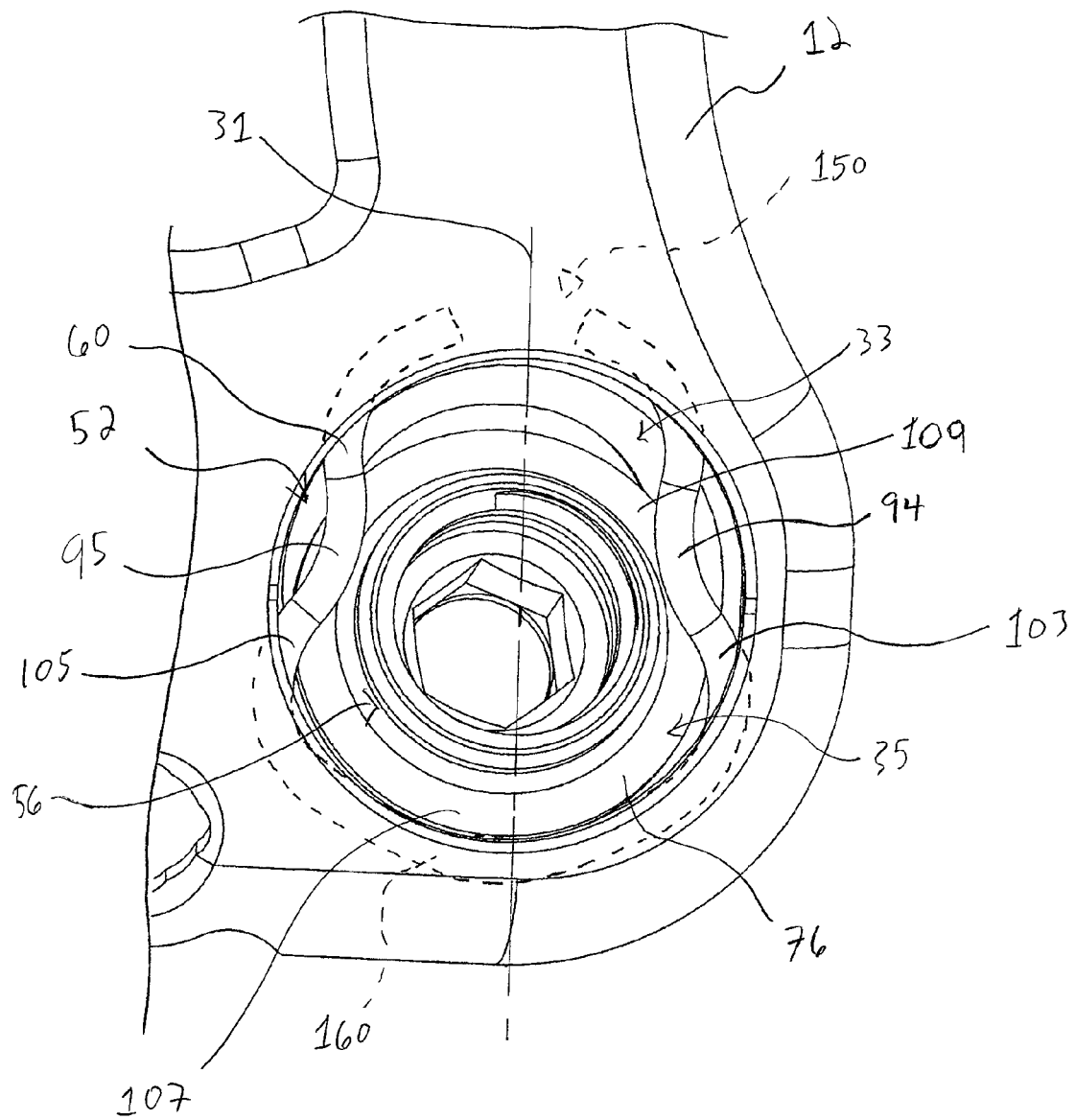
FIG. 2 is an enlarged, plan view of one of the throughbores of the bone plate system of FIG. 1 showing arms of the retainer extending along the throughbore and ends of the resilient retainer in phantom.

In FIGS. 1-15, a bone plate system 10 in accordance with one form of the present invention is shown. The bone plate system 10 includes a bone plate 12 having a throughbore 52 for receiving a bone anchor 56 and a retainer 60 disposed in the throughbore 52 for resisting back-out of the bone anchor 56, as shown in FIG. 2. The retainer 60 has interference portions 94, 95 that deflect apart as the bone anchor 56 is inserted into the throughbore 52 and resiliently return to an interference position above an enlarged head 76 of the bone anchor 56 once the head 76 is seated within the throughbore 52 to resist back-out of the bone anchor 56 from the throughbore 52. The retainer 60 has ends 150, 160 held within the bone plate 12 and the interference portions 94, 95 extend between the ends 150, 160 along opposite sides of the throughbore 52. The throughbore 52 has a length along an axis 31 and a pair of opposite axial end portions 33, 35. The axial portion 35 and the bone anchor head 76 are sized relative to each other to allow the bone anchor 56 to extend obliquely in the throughbore 52 with a raised portion 107 of the bone anchor head 76 extending level with or above the retainer 60 in the axial portion 35 of the throughbore 52 while a lowered portion 109 of the bone anchor head 76 is disposed below the interference portions 94, 95 in the axial portion 33 of the throughbore 52. Further, transverse portions 103, 105 of the retainer 60 extend away from the interference portions 94, 95 to provide room for the raised portion 107 of the bone anchor head 76 when the bone anchor head 76 is seated in the bore 52 and the bone anchor 56 extends obliquely in the bore 52. By allowing the raised portion 107 of the bone anchor head 76 to extend to a height level with or above the retainer 60, the thickness of the bone plate 12 can be reduced since the entirety of the bone anchor head 76 does not need to be disposed below the retainer 60.

Figure 3:
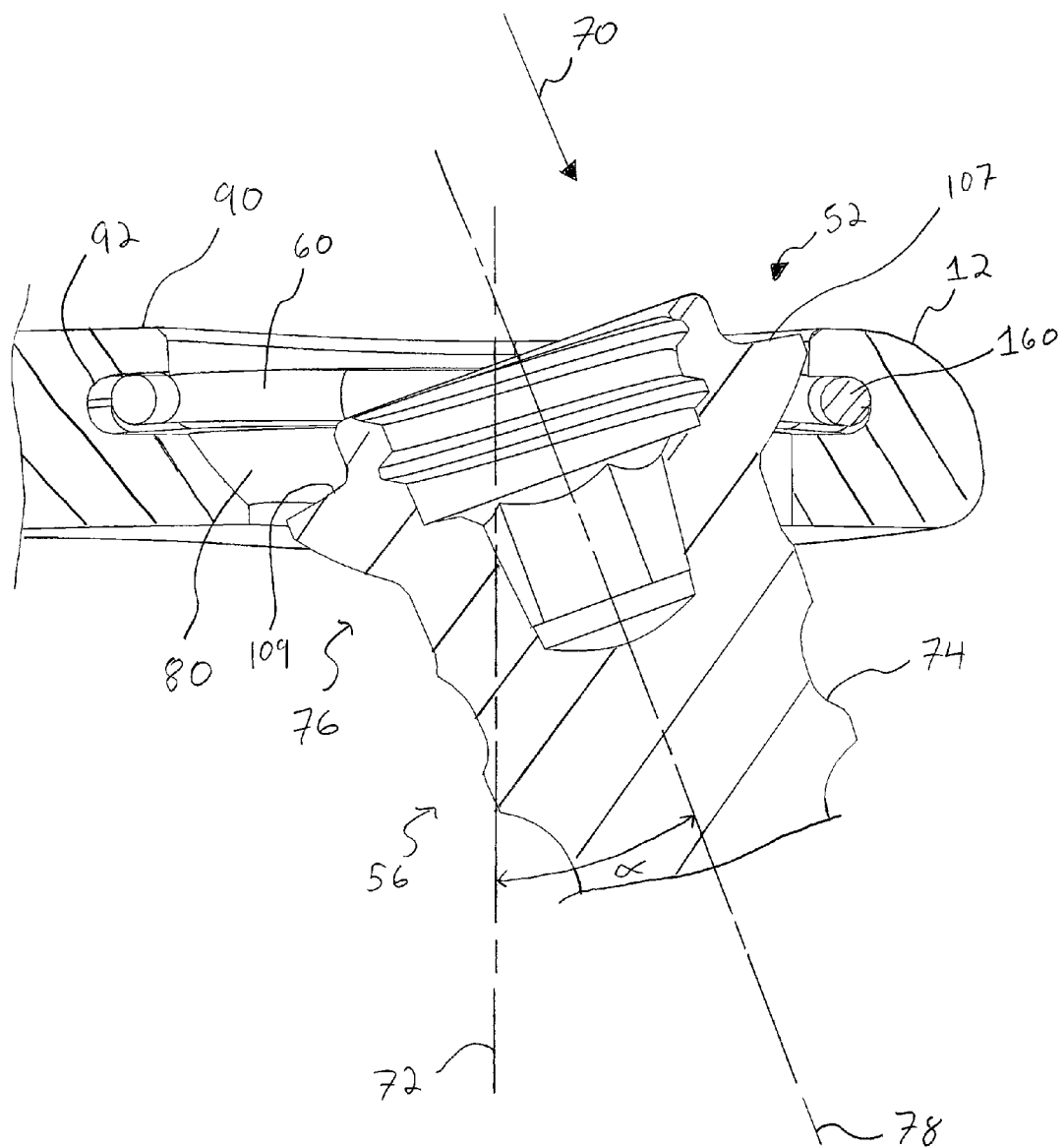
FIG. 3 is a cross-sectional view of the bone plate system of FIG. 1 taken across line 3-3 in FIG. 1 showing one of the bone anchors seated in one of the throughbores.
Figures 4, 5:
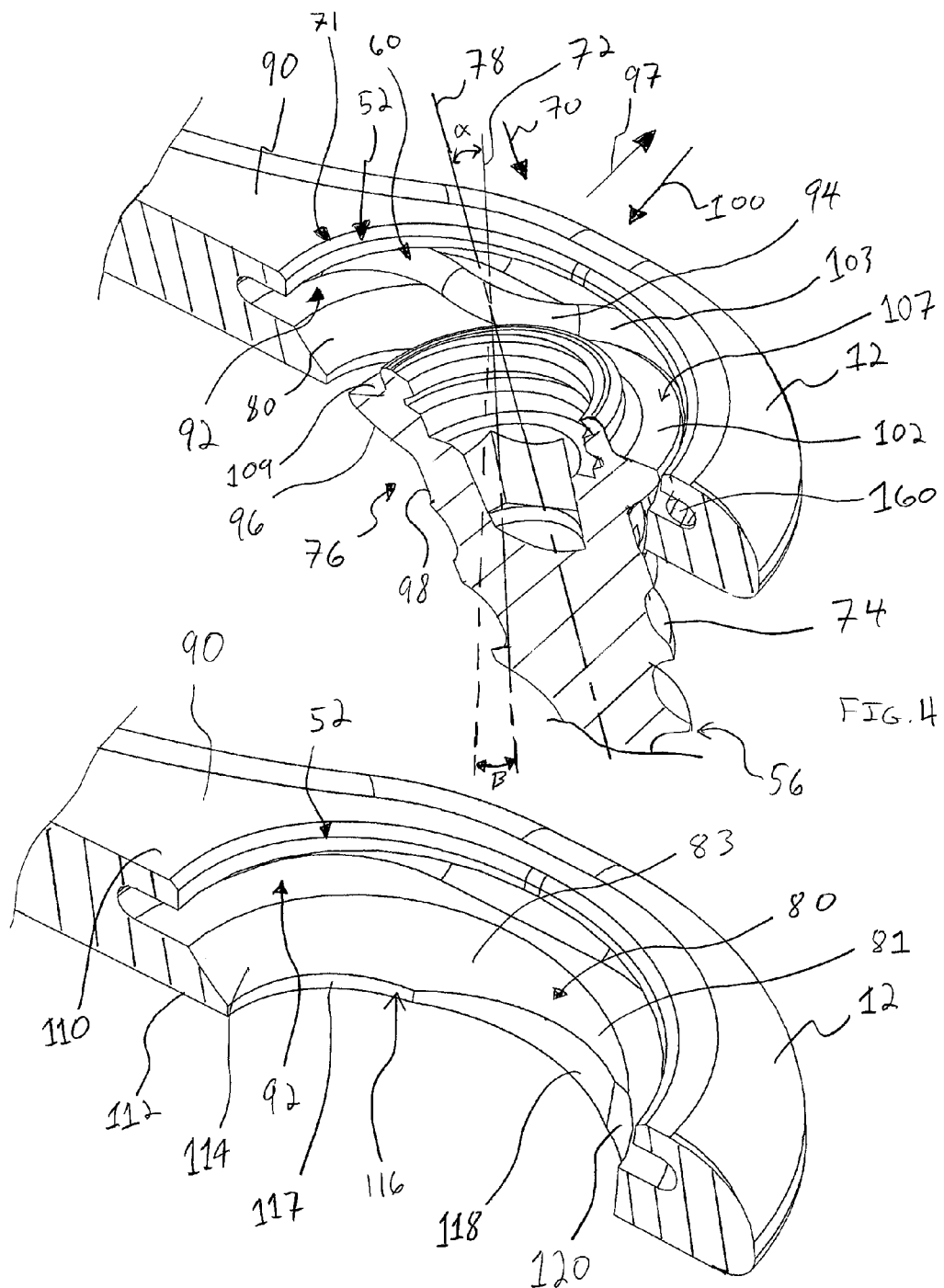
FIG. 4 is a fragmented cross-sectional view of the bone plate system of FIG. 1 similar to FIG. 3 showing a portion of a resilient retainer extending over the bone anchor to resist back-out.
FIG. 5 is a enlarged view similar to FIG. 4 with the retainer and the bone anchor removed to show a groove in the bore wall.
Figure 6:
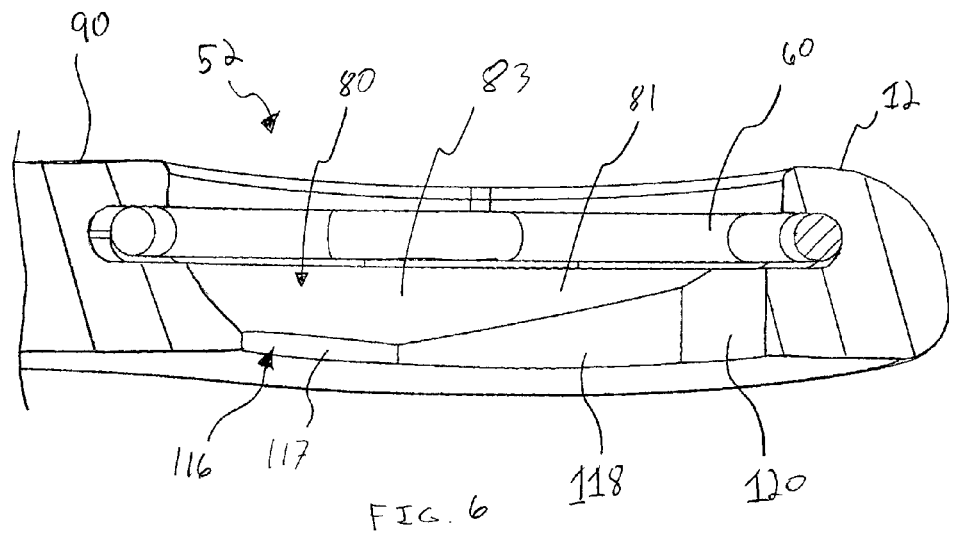
FIG. 6 is a cross-sectional view of the bone plate system of FIG. 1 similar to FIG. 3 with the bone anchor removed to show a profile of a throughbore seat.

More specifically, the bone anchor 56 may be driven into the throughbore 52 at an oblique angle α relative to a bore central axis 72 until the head 76 of the bone anchor 56 engages a seat 80 of the throughbore 52, as shown in FIG. 3. The seat 80 has a narrow or shallow portion 81 and a wide or deep portion 83 that engage the bone anchor head 76, as shown in FIG. 5. The shallow portion 81 positions the raised portion 107 higher within the bore 52 than the wide portion 83 positions the lowered portion 109 such that the raised portion 107 extends above the retainer 60, as shown in FIG. 4. The lowered portion 109, however, extends below the interference portions 94, 95 such that the resilient retainer 60 still resists back-out of the bone anchor 56 via engagement between the interference portions 94, 95 and the lowered portion 109 even with the raised portion 107 extending above the retainer 60. Further, the transverse portions 103, 105 of the retainer bow outwardly apart from one another and are disposed on either side of the raised portion 107 and out of the way of the bone anchor head 76 seated in the throughbore 52. In this manner, the interference portions 94, 95 can resiliently return to their interference position once the bone anchor head 76 is seated within the bore 52 without contact between the transverse portions 103, 105 and the bone anchor head 76 limiting movement of the interference portions 94, 95.

Returning to FIG. 1, the bone plate 12 is preferably made of biocompatible materials, such as titanium, titanium alloy, or stainless steel. The bone plate 12 has a pair of upper dynamized throughbores 14, 16 configured to receive bone anchors 18, 20 therein and permit the anchors 18, 20 to translate within the bores 14, 16 along the length of the bone plate 12. Resilient retainers 22, 24 are positioned within the bores 14, 16 and resist back-out of bone anchors 18, 20 as the anchors 18, 20 translate along the bores 14, 16. The bone plate 12 also includes a pair of intermediate dynamized throughbores 30, 32 that receive bone anchors 34, 36 and which have a length that is less than the length of the upper dynamized bores 14, 16. Resilient retainers 38, 40 restrict back-out of the anchors 34, 36 along the length of the throughbores 30, 32 in a manner similar to the retainers 22, 24. Bone plate 12 further comprises a pair of lower non-dynamized throughbores 50, 52 that do not permit translation of bone anchors 54, 56. Instead, the bone anchors 54, 56 are fixed against translation and retainers 58, 60 resist back-out of the bone anchors 54, 56 from the throughbores 50, 52. The throughbores 14, 16, 30, 32, 50, and 52 may all generally permit polyaxial insertion to provide flexibility during installation of the bone plate system 10. The bone plate 12 has windows 62 and openings 64 sized to receive portions of a tool (not shown) for positioning the bone plate 12 during surgery.

As shown in FIG. 3, the bone anchor 56 is driven into the lower non-dynamized throughbore 52 in an oblique direction 70 at an oblique angle α relative to the bore central axis 72 to drive a shank 74 of the bone anchor 56 into a bone (not shown) disposed below the bone plate 12. Driving the bone anchor 56 in direction 70 also engages the head 76 of the bone anchor 56 against the seat 80 of the bone plate 12 and fixes the bone plate 12 to the bone. In the lower non-dynamized throughbores 50, 52, the bone plate system 10 preferably provides a bone anchor insertion angle α between the bore central axis 72 and a longitudinal axis 78 of the bone anchor 56 of up to approximately 20° along the length of the bone plate 12. In the illustrated embodiment, the remaining bores 14, 16, 30, 32 provide a smaller range of bone anchor insertion angles, as will be discussed in greater detail below.

As shown in FIG. 4, the bone plate 12 has a retention structure for holding the retainer 60 in the bore 52 of the bone plate 12. For this purpose, a bore wall 90 extends about the bore 52 with a groove 92 therein sized to receive portions of the retainer 60. As the bone anchor 56 is inserted into the bore 52 in direction 70, the shank 74 and the head 76 cammingly engage interference portions 94, 95 (see FIG. 11) of the retainer 60 so as to push the retainer interference portions radially outward in radially outward directions 97, 99 toward the bore wall 90. When the bone anchor head 76 is seated within the bore 52, the interference portions 94, 95 resiliently return in radially inward directions 100, 101 so as to extend over the bone anchor head 76 in interference therewith. The interference portions 94, 95 extend over the anchor head 76 in overlapping relation so as to cross annular surface 102 of the bone anchor 56 such that the interference portions 94, 95 restrict back-out of the bone anchor 56. As illustrated, a generally elliptical opening 71 opens into the bore 52 and the interference portions 94, 95 may extend across the opening 71 in a manner similar to chords of an ellipse.

The transverse portions 103, 105 extend away from the interference portions 94, 95 and into the groove 92 (see FIG. 11). As the bone anchor 56 enters the throughbore 52 at an angle α, the shank 74 and/or the head 76 may cam the interference portions 94, 95 and/or the transverse portions 103, 105 toward the groove 92 and out of the path of the bone anchor 56, as shown in FIG. 4. The transverse portion 103 is spaced radially outward from the raised portion 107 when the bone anchor head 76 is seated at angle α within the throughbore 52. The interference portions 94, 95 are disposed above at least a portion of the bone anchor head annular surface 102 to be in interference therewith and restrict back-out of the bone anchor 56 from the throughbore 52.

With reference to FIGS. 4 and 5, the bore wall 90 includes inwardly extending upper and lower sections 110, 112 that extend around the bore 52 and define the groove 92 therebetween. The seat 80 includes a seating surface 114 that is complimentary to a curved surface 96 of the bone anchor head 76 and permits the bone anchor head 76 to seat within the bore 52 at a range of bone anchor insertion angles. The engagement between the curved seating surface 114 and the bone anchor head lower surface 96 permits the bone anchor 56 to be polyaxially driven into and seated in the throughbore 52. Further, the engagement between the curved surfaces 96, 114 may permit relative movement therebetween so the bone anchor 56 can rotate relative the bone plate 12 and permit a bone engaged with the anchor 56 to subside.

As shown in FIG. 5, the seat 80 includes a collar portion 116 that generally defines a lower portion of the bore 52 and engages the bone anchor shank 74 to restrict an insertion angle α of the bone anchor 56 in the cephalad/caudal (toward the head or feet) plane to a range of approximately −10° to approximately +20° from the bore central axis 72. The collar portion 116 also restricts an insertion angle β of the bone anchor 56 in the medial/lateral (toward the center or side) plane to a range of approximately −5° to approximately +5° from the bore central axis 72.

The collar portion 116 includes substantially vertical walls 117, 118, 120 that engage the bone anchor shank 74 and neck 98 and restrict the angle at which the bone anchor 56 may extend within the bore 52. For example, with reference to FIGS. 6 and 7, driving the anchor 56 into the bore 52 at angle α seats the lower curved surface 96 of the bone anchor head 76 upon both the narrow portion 81 and the wide portion 83 of the seat 80. The seat 80 and the lower curved surface 96 of the bone anchor head 76 preferably have spherical profiles with a substantially similar radius of curvature to permit the bone anchor 56 to engage the seat 80 throughout a range of insertion angles of the bone anchor 56.

Figure 7:
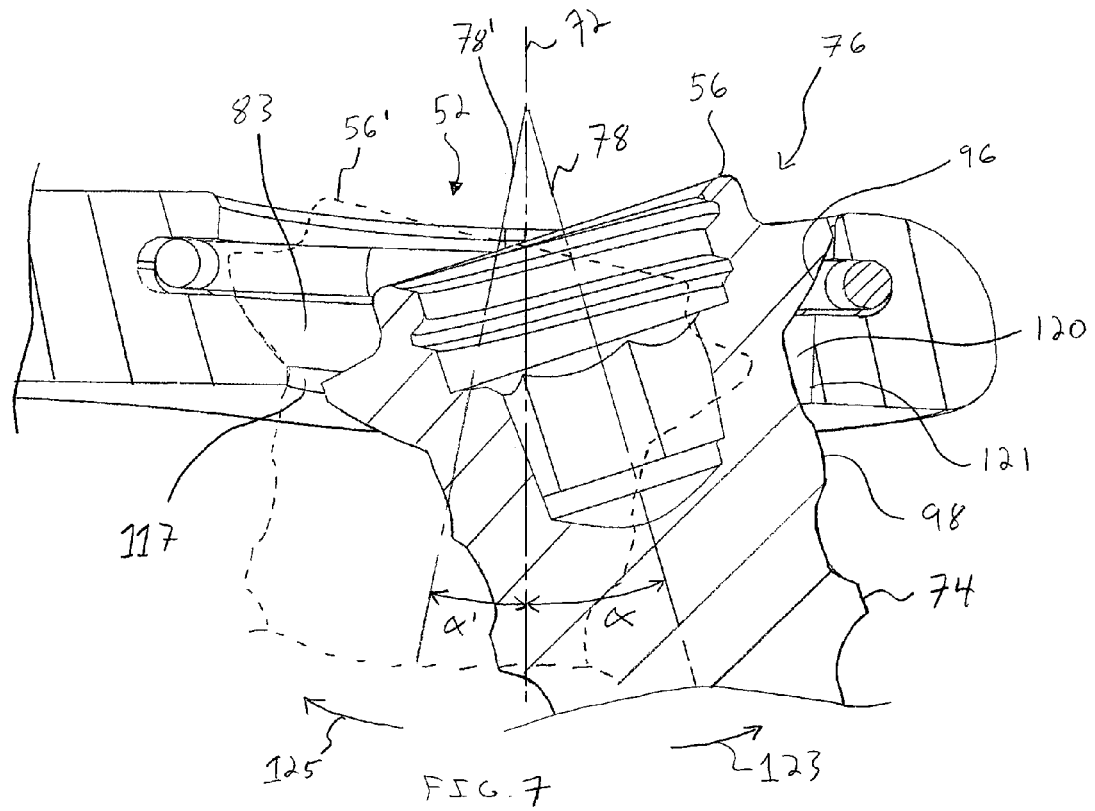
FIG. 7 is a cross-sectional view of the bone plate system of FIG. 1 similar to FIG. 6 showing the bone anchor seated in the throughbore at a maximum angle toward an adjacent end of the bone plate and, in phantom, the bone anchor seated in the throughbore at a maximum angle toward a center of the bone plate.

The walls 118, 120 are radially recessed such that the walls 118, 120 provide clearance for the bone anchor shank 74 to extend at oblique angles relative to the bore central axis 72 in the cephalad/caudal and medial/lateral planes. As shown in FIG. 7, the wall 120 has a lower portion 121 that engages the bone anchor shank 74 and/or neck 98 and restricts the bone anchor 56 from being inserted into the bore 52 at an insertion angle greater than maximum oblique angle α. Once the bone anchor head 76 is engaged with the seat 80, the walls 118, 120 also restrict rotation of the anchor 56 in direction 123 beyond angle α to limit post-operative rotation of the bone anchor 56. At the other end of the bore 52, the wide portion 83 of the seat 80 extends radially inward farther than the narrow portion 81 (see FIG. 10). As shown by reference numeral 56' in FIG. 7, subsidence of the bone engaged with bone anchor 56 may rotate the anchor 56 in direction 125 until the anchor 56 extends at a maximum oblique angle α' relative to the bore axis 72. The wide portion 83, and the clearance wall 117 extending therebelow, restrict rotation of the bone anchor 56 in direction 125 beyond the angle α' and thereby restrict subsidence of a bone engaged with bone anchor 56. In the illustrated form, angle α is approximately 20° and angle α' is approximately 10°.

Figure 8:
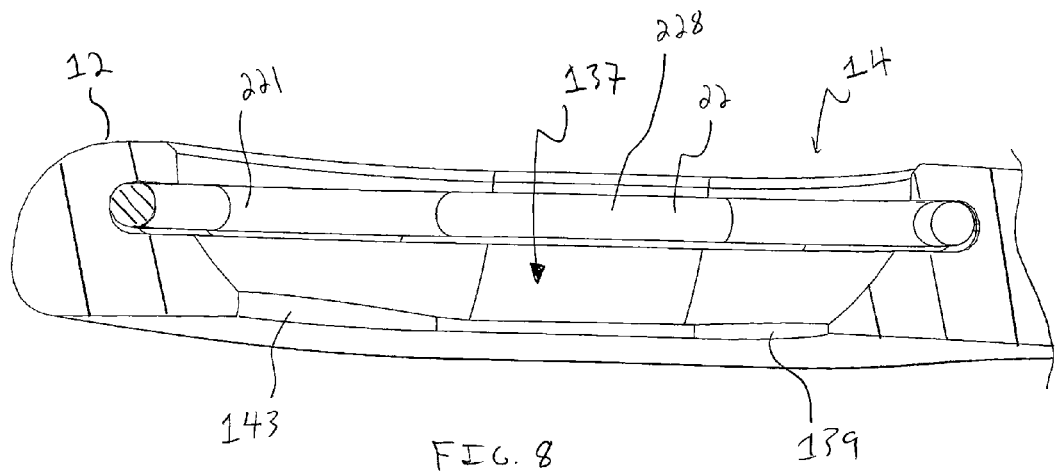
FIG. 8 is a cross-sectional view of the bone plate system of FIG. 1 taken along line 8-8 in FIG. 1 with the associated bone anchor removed to show a profile of a throughbore seat.
Figure 9:
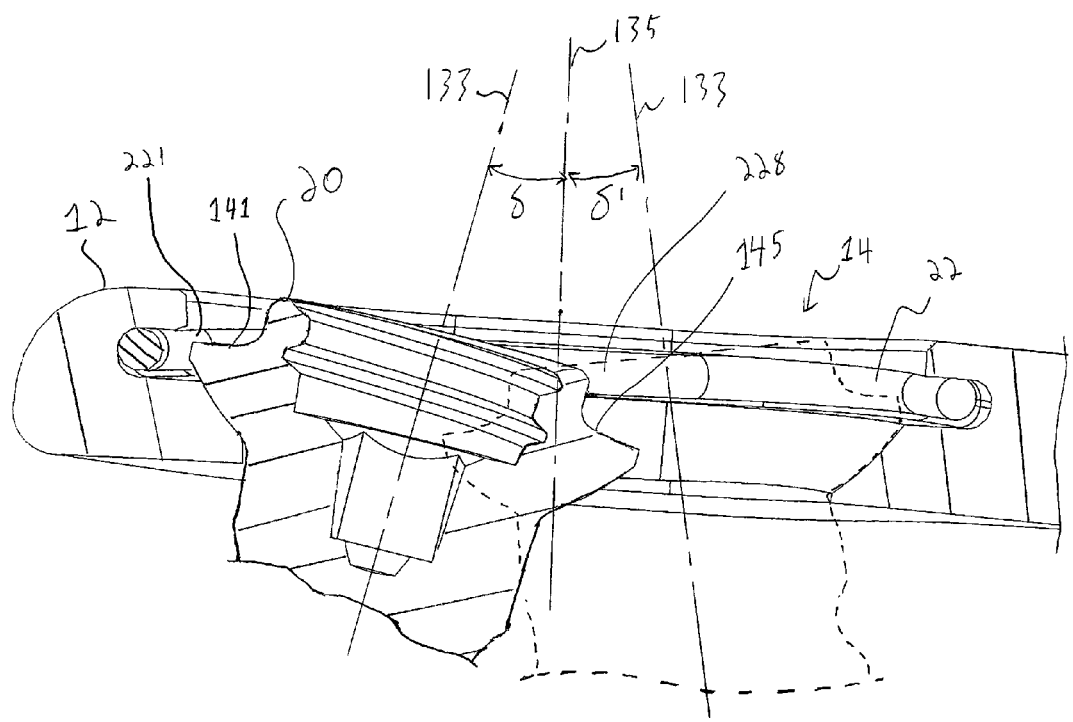
FIG. 9 is a cross-sectional view of the bone plate system of FIG. 1 similar to FIG. 8 showing the bone anchor seated in the throughbore at one end of the throughbore at a maximum angle toward an adjacent end of the bone plate and, in phantom, the bone anchor seated at the other end of the throughbore at a maximum angle toward the center of the bone plate.

Unlike the bore 52, the elongated bore 14 has similar maximum oblique angles δ, δ' between a longitudinal axis 133 of the bone anchor 20 and a central bore axis 135 in the cephalad/caudal plane, as shown in FIGS. 8 and 9. The bore 14 has a seat 137 with a substantially uniform width around the bore 14. The seat 137 has a lower wall 139 extending around the bore 14 for engaging and restricting the bone anchor insertion angle beyond angle δ and rotational subsidence of the bone anchor 20 beyond angle δ'. As is apparent, the seat 137 lacks radially recessed walls, like the walls 118 and 120 of seat 80, which permit the bone anchor 20 to extend at a greater angle in one direction than in another direction along the length of the bone plate 12. The seat 137 may include a relatively small cutout 143 that permits the bone anchor 20 to extend at angle δ and compensates for the curvature of the bone plate 12. Further, the seat 137 and the lower wall 139 permits a raised portion 141 of the bone anchor 20 to be level with the bone plate engaging portions 219, 221 of the retainer 22 and a lowered portion 145 of the bone anchor 20 to be disposed below interference portions 226, 228 of the retainer 22 when the bone anchor 20 extends obliquely in the bore 14 (see FIGS. 8 and 9). In the illustrated form, angles δ and δ' are both approximately 10°.

The bores 14, 16, 30, 32 each provide bone anchor insertion angles in the range of approximately −10° to approximately +10° in the cephalad/caudal plane and approximately −5° to approximately +5° in the medial/lateral plane. In an alternative form shown in FIG. 13B, the bone anchor head 76A has an enlarged cylindrical section 199A rather than the curved surface 96 and the bone plate seat 80 has a shape complimentary to the cylindrical outer profile such that the bone anchor 56A is restricted to seating within the throughbore 52 at a predetermined angle, e.g., +10° in the cephalad/caudal plane, and +5° in the medial/lateral plane. The complimentary shape of the bone plate seat 80 also inhibits pivoting of the bone anchor 56A once the bone anchor 56A is engaged with the seat 80.

Turning to FIGS. 10 and 11, a cross-sectional view of the bore wall 90 surrounding the bore 52 is shown. The bore wall 90 includes pairs of transverse end walls 130, 132, 134, and 136. The bore wall 90 also includes a pair of opposed side walls 138, 140 separated from the transverse end walls 134, 136 by corners 142, 144. The transverse end walls 130, 132, 134, 136 are disposed between the inwardly extending sections 110, 112 (see FIG. 5) of the bore wall 90 and define a height of the groove 92. To position the retainer 60 within the groove 92, as shown in FIG. 11, the retainer 60 has an open end portion 150 including a pair of spaced ends 152, 154 separated by a gap spacing 156. The spaced ends 152, 154 are deflected toward each other to shift the retainer 60 to a collapsed position before a closed end portion 160 of the retainer is inserted into the bore 52 and positioned within the groove 92. The open end portion 150 is inserted into the groove 92 and the spaced ends 152, 154 are released. The spaced ends 152, 154 resiliently expand apart to fix the retainer 60 within the groove 92. In a preferred approach, the bone plate system 10 is preassembled with the retainers disposed in respective throughbores.

With the retainer 60 in the groove 92, the spaced ends 152, 154 abut the transverse end walls 130, 132 and retainer straights 162, 164 abut the transverse end walls 134, 136, as shown in FIG. 11. In one approach, the bone anchor 56 is inserted into the throughbore 52 and rotated in direction 166 to drive the bone anchor 56 into a bone (not shown). Contact between the rotating bone anchor 56 and the retainer 60 may cause the retainer 60 to tend to rotate in direction 166. To resist this rotation, the retainer straight 164 engages the transverse extending wall 136 and a bend 168 of the retainer 60 engages the corner 142 of the bore wall 90. Similarly, if the bone anchor 56 is rotated in direction 170 to remove the bone anchor 56 from the bone, the contact between the bone anchor 56 and the retainer 60 may cause the retainer 60 to tend to rotate in direction 170. To resist this rotation, the retainer straight 162 engages the transverse end wall 134 and a bend 172 of the retainer 60 engages the corner 144 of the bore wall 90. Further, inserting the bone anchor 56 into the bore 52 causes the shank 74 and the head 76 to cam the interference portions 94, 95 radially outward in directions 97, 99, as discussed above. This causes the spaced ends 152, 154 of the retainer 60 to move in directions 178, 180 along the transverse end walls 130, 132.

Figures 12, 13A:
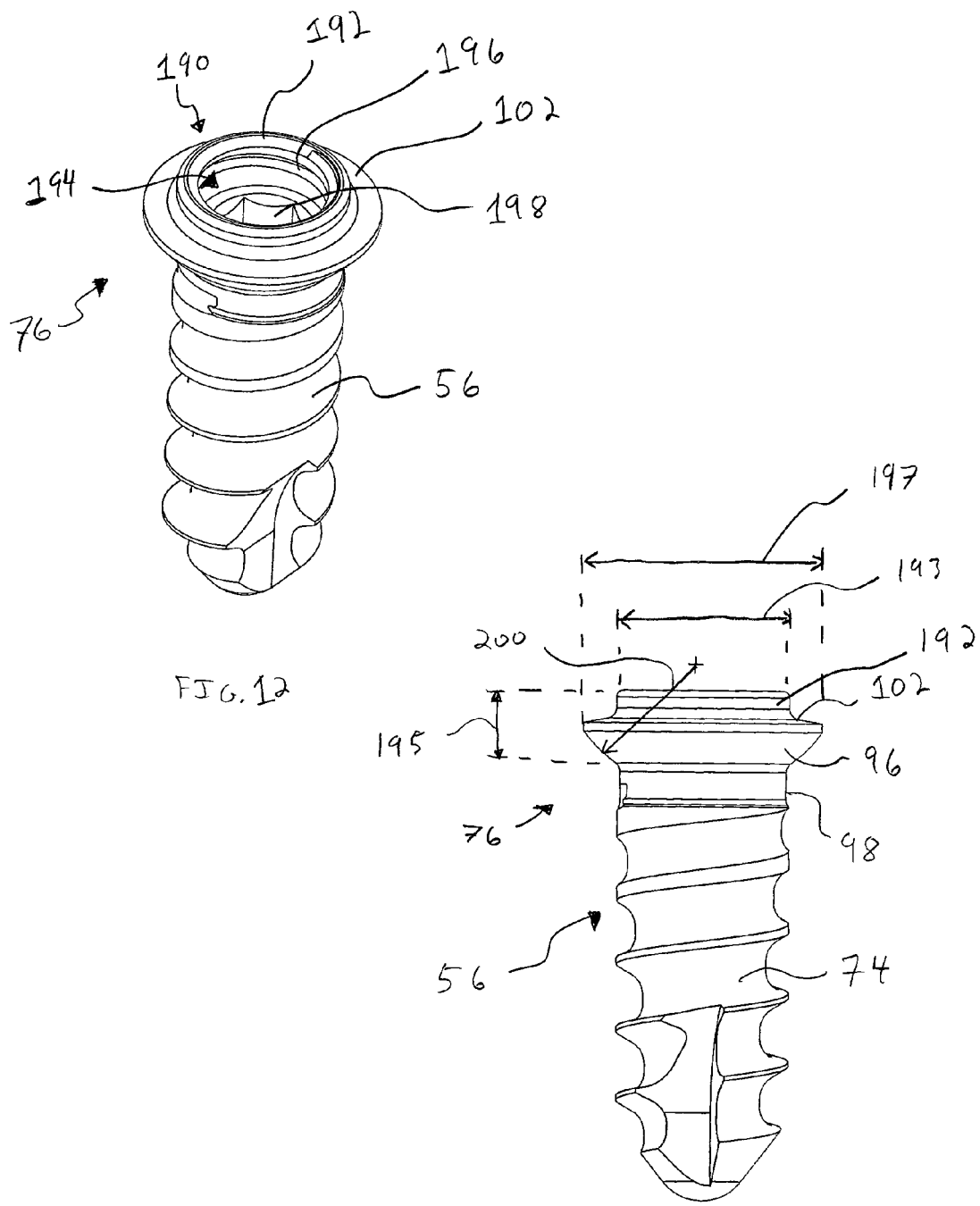
FIG. 12 is a perspective view of a bone anchor of the bone plate system of FIG. 1 showing a tool-receiving bore of the bone anchor.
FIG. 13A is a side elevational view of the bone anchor of FIG. 12 showing an outer profile of the bone anchor head.
Figure 13B:
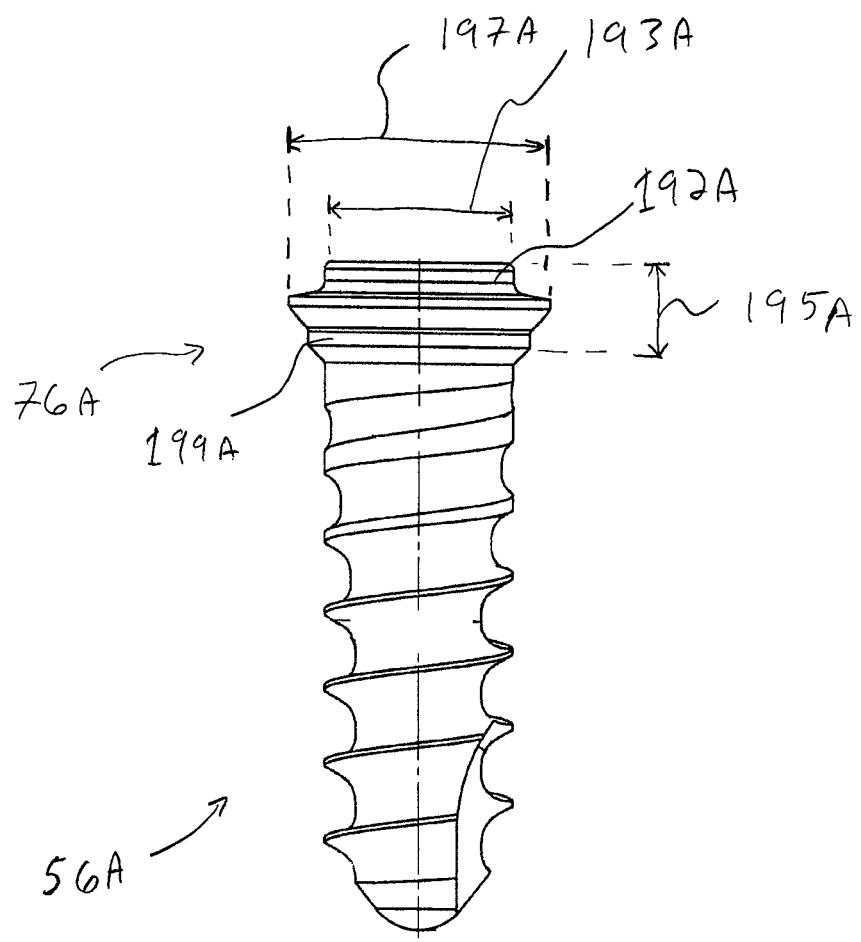
FIG. 13B is a side elevational view of another bone anchor showing an outer profile of the bone anchor head.

Turning to FIGS. 12-13B, further details of the bone anchor 56 are illustrated. Specifically, the head 76 includes a collar 190 comprising an annular wall 192 extending around a tool receiving bore 194. The collar 190 includes threads 196 used to secure the bone anchor 56 to a tool and a hex recess 198 for receiving a drive portion of the tool. The annular wall 192 may have an outer diameter 193 in the range of approximately 0.12 inches to approximately 0.18 inches, preferably approximately 0.158 inches. In one form, the outer diameter 193 is slightly larger than the interference distance 230 of the retainer 22 (see FIG. 14A) when the retainer 22 is disposed in the elongate throughbore 14 such that the annular wall 192 of the bone anchor 20 slightly biases the respective interference portions 226, 228 apart as the bone anchor 20 travels along the elongate bore 14. The curved surface 96 may have a radius 200 in the range of approximately 0.11 inches to approximately 0.16 inches, preferably 0.135 inches. The head 76 may have a height 195 in the range of approximately 0.06 inches to approximately 0.09 inches, preferably approximately 0.075 inches. The bone plate 12, by contrast, may have a thickness adjacent the throughbore 52 in the range of approximately 0.072 inches to approximately 0.108 inches, preferably 0.09 inches. The head 76 may have an outer diameter 197 in the range of approximately 0.17 inches to approximately 0.25 inches, preferably 0.218 inches. In an alternative form, the head 76 lacks the annular wall 192 such that the annular surface 192 generally defines the uppermost portion of the head 76. The bone anchor 56 is preferably made from titanium, but may be made of another biocompatible material such as titanium alloy or stainless steel.

As shown in FIG. 13B, bone anchor 56A is similar to the bone anchor 56 except that the bone anchor 56 is a fixed angle screw as discussed above. In this embodiment, the bone anchor 56A has an annular wall 192A with an outer diameter 193A in the range of approximately 0.12 inches to approximately 0.18 inches, preferably 0.158 inches. The head 76A has a height 195A in the range of approximately 0.05 inches to approximately 0.09 inches, preferably 0.07 inches. Further, the head 76A has an outer diameter 197A in the range of approximately 0.17 inches to approximately 0.25 inches, preferably 0.218 inches.

Figure 14A:
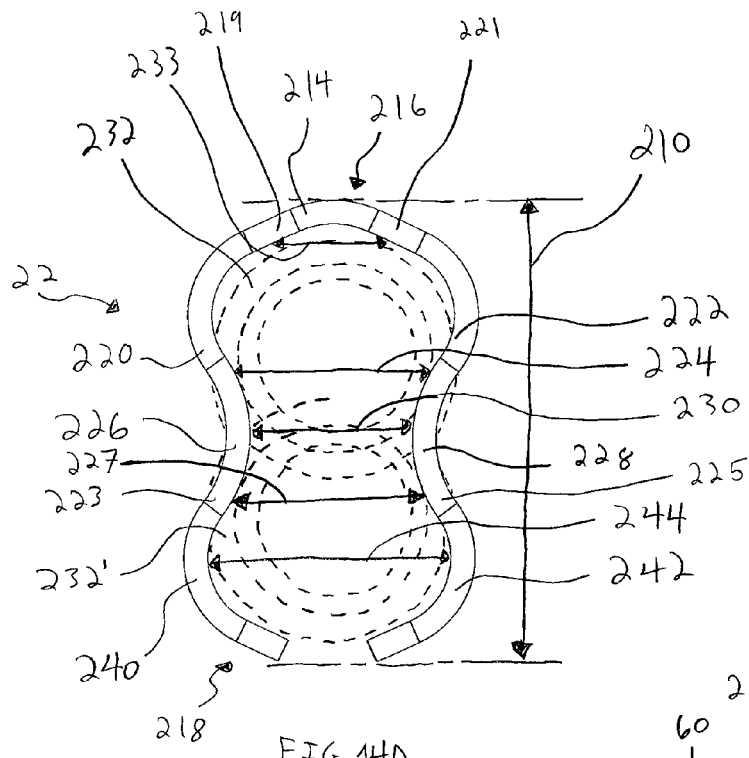
FIG. 14A is a plan view of a retainer for a dynamized bore of the bone plate system of FIG. 1 showing the retainer disposed above an associated bone anchor shown in phantom as the bone anchor travels along the dynamized bore.
Figure 15:
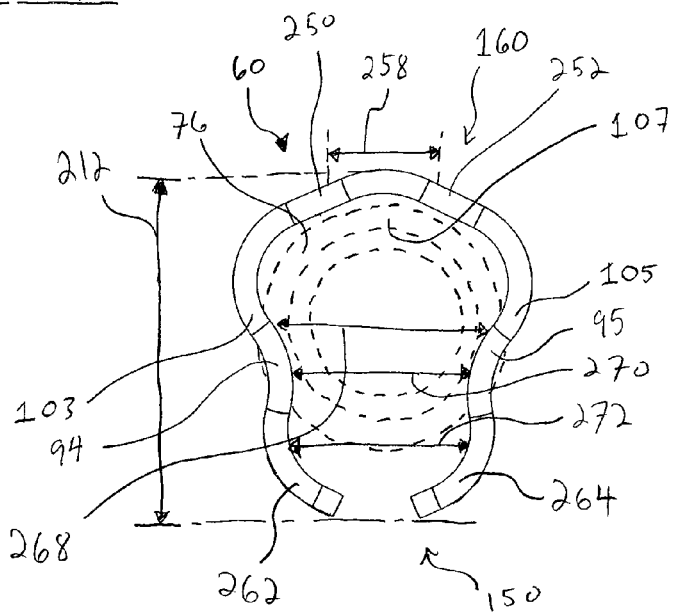
FIG. 15 is a plan view of a retainer for a non-dynamized bore of the bone plate system of FIG. 1 showing the retainer disposed above an associated bone anchor shown in phantom.
Figure 14B:
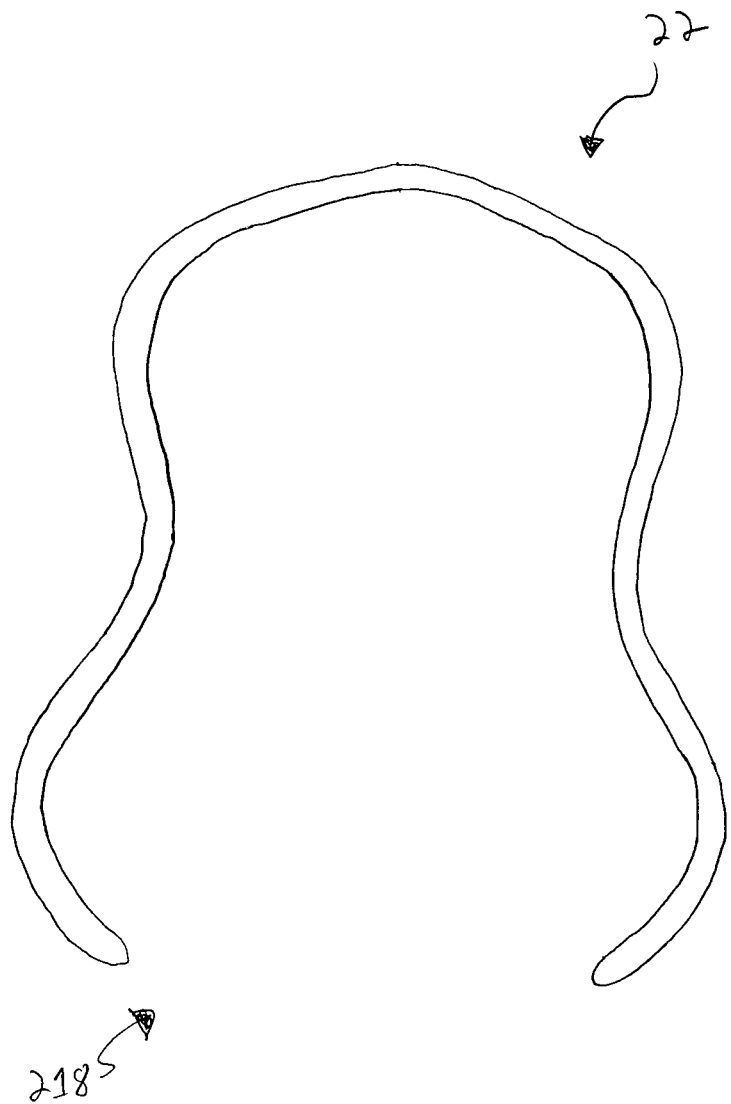
FIG. 14B is a plan view of the retainer of FIG. 14A showing the retainer in an expanded configuration.

In FIGS. 14A and 15, the resilient retainer 22 for the dynamized bore 14 and the resilient retainer 60 for the non-dynamized bore 52 are illustrated disposed above respective bone anchor heads 232, 76 (see FIG. 1) shown in phantom for clarity. The retainers 22, 60 are shown in FIGS. 14A and 15 as they would appear when positioned within respective bores 14, 52. The resilient retainers 22, 60 may be larger than the respective bores 14, 52 such that the retainers 22, 60 are in a deflected configuration when positioned within the bores 14, 52. For example, FIG. 14B illustrates the retainer 22 in an expanded configuration when the retainer 22 is removed from the bore 14. The retainer 22 has open end portion 218 open a greater amount than when the retainer 22 is positioned within the throughbore 14, as shown in FIG. 14A. The retainers 22, 60 are preferably made by bending elongate Nitinol wires into the desired retainer shape. The retainer 22, 60 may alternatively be made of titanium, titanium alloy, stainless steel, or other biocompatible materials.

The retainer 22 has a thin body 214 comprising a closed end portion 216 and an open end portion 218. A pair of bone plate engaging portions 219, 221 extend away from the closed end portion 216 and are separated from each other by a distance 233. The closed end portion 216 and the bone plate engaging portions 219, 221 are received within a groove of the throughbore 14 similar to the groove 92 of the throughbore 52 and keep the retainer 22 within the bore 14. A pair of transverse portions 220, 222 extend inward from the bone plate engaging portions 219, 221 and are spaced from each other by a distance 224 sized to accommodate a raised portion of a bone anchor head 232 (see FIG. 1) between the transverse portions 220, 222 and the closed end 216 (see FIG. 9) of the retainer 22. The retainer 22 includes a pair of interference portions 226, 228 spaced from each other by an interference distance 230 sized to resist back-out of the bone anchor head 232. The interference portions 226, 228 extend along the retainer 22 a length sufficient to be disposed above the bone anchor head 232 whether the bone anchor 18 is at one end of the dynamized bore 14, as indicated by reference numeral 232 in FIG. 14A, or at the other end of the dynamized bore 14, as indicated by reference numeral 232' in FIG. 14A. The retainer 22 may also have bone plate engaging portions 240, 242 between the interference portions 226, 228 and the open end portion 218 that are spaced from each other by a distance 244. A pair of transverse portions 223, 225 extend inward from the bone plate engaging portions 240, 242 and are spaced by a distance 227 sized to accommodate a raised portion of the bone anchor head 232 between the transverse portions 223, 225 and the open end portion 218 (see FIG. 9). Like the bone plate engaging portions 219, 221, the bone plate engaging portions 240, 242 and the open end portion 218 are received within a groove of bore 24 and keep the retainer 22 within the throughbore 14. The positions of the distances 233, 224, 230, 227, and 244 along the retainer 22 are exemplary and not intended to be limiting. The distances 233, 224, 230, 227, and 244 may generally extend between the respective portions of the retainer 22 at any position along the length of the respective portions.

In FIG. 15, the resilient retainer 60 is illustrated with the approximate position of the bone anchor head 76 within the bore 52 illustrated in dashed lines. The retainer 60 is similar to the retainer 22 and includes bone plate engaging portions 250, 252, transverse portions 103, 105, interference portions 94, 95, and bone plate engaging portions 262, 264, as well as similar associated distances 258, 268, 270, 272. The clearance distance 268 is sized to provide clearance from the raised portion 107 of the bone anchor head 76 (see FIG. 4) when the bone anchor head 76 is seated at an angle within the throughbore 52. One difference between the retainer 60 and the retainer 22 is that the retainer 60 has a wide, closed end portion 160 and a narrow, open end 150 whereas the ends 216, 218 of the retainer 22 are similarly sized.

A bone plate system 410 in accordance with another form of the present invention is shown in FIGS. 16-21. The bone plate system 410 is similar to the bone plate system 10 and includes a bone plate 412 having a resilient retainer 416 for resisting back-out of a bone anchor 418 from the bone plate 412. One difference between the bone plate system 410 and the bone plate system 10 is that the bone plate 412 includes only non-dynamized pairs of throughbores 413, 414, 415. The bores 413, 415 permit bone anchor insertion angles in a range of approximately −10° to approximately 20° in the cephalad/caudal plane and a range of approximately −5° to approximately +5° in the medial/lateral plane. The pair of throughbores 414 permit bone anchor insertion angles in a range of approximately −10° to approximately +10° in the cephalad/caudal plane and a range of approximately −5° to approximately +5° in the medial/lateral plane. Further, the bone plate 412 has windows 420 with tool-engaging features 422 for accommodating different shapes of tools than the windows 62 of the bone plate 12.

Figure 18:
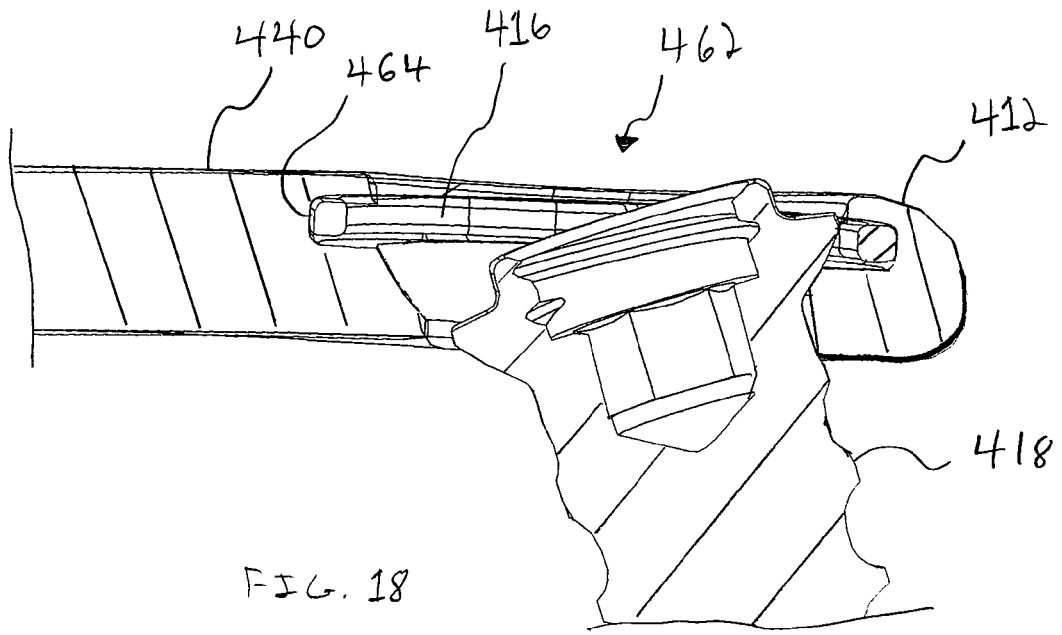
FIG. 18 is an enlarged cross-sectional view of the bone plate system of FIG. 16 taken along line 18-18 in FIG. 16 showing a bone anchor seated within an associated throughbore.
Figure 19:
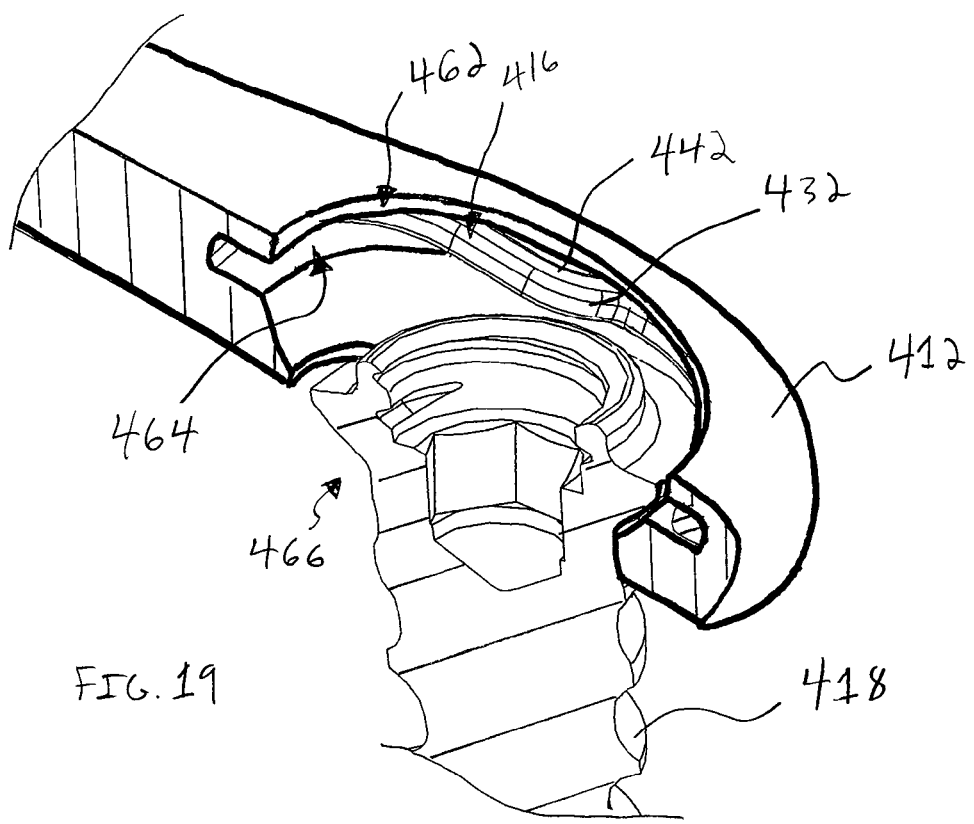
FIG. 19 is an enlarged cross-sectional perspective view of the bone plate system of FIG. 16 similar to FIG. 18 showing a portion of the resilient retainer extending over the bone anchor to resist back-out.
Figure 22:
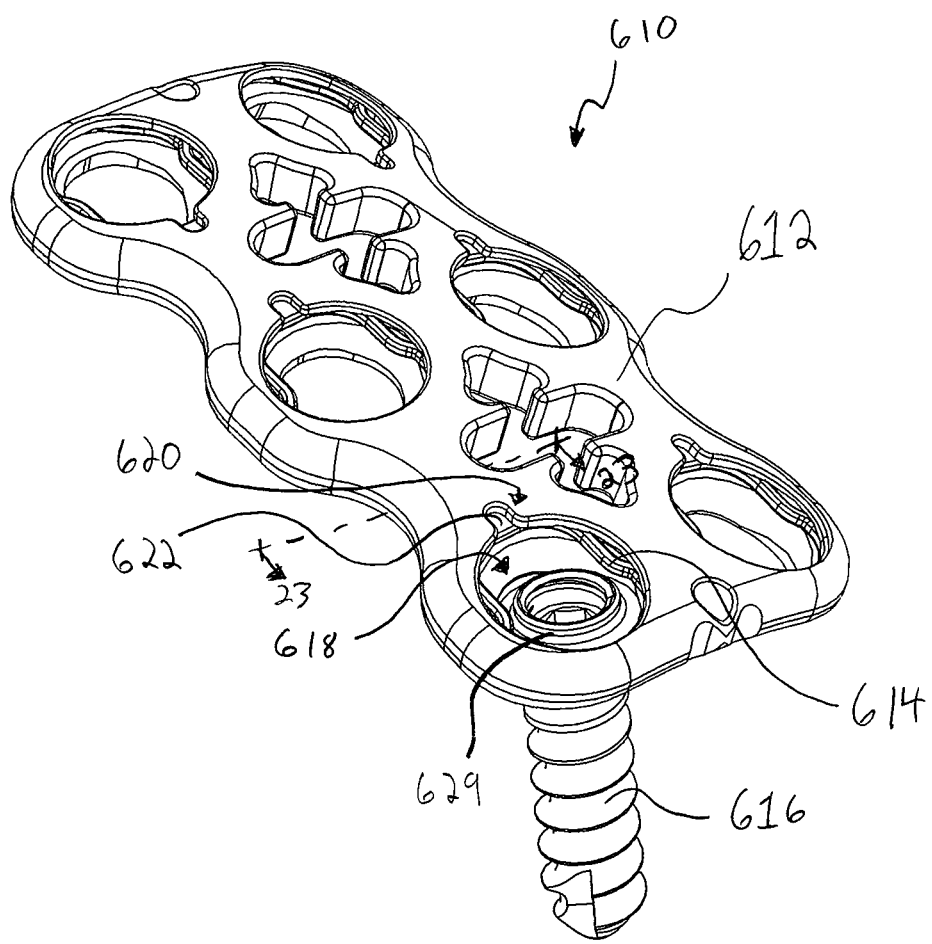
FIG. 22 is a perspective view of a bone plate system in accordance with another form of the present invention having all but one bone anchor removed from the bone plate.

Another difference between the bone plate system 410 and the bone plate system 10 is the shape of the resilient retainer 416. The resilient retainer 416 is preferably laser cut from sheet stock, such as Nitinol or titanium sheet stock. The resilient retainer 416 has an expanded configuration that is less expanded than the retainer 22 (see FIG. 14B) such that the retainer 416 is deflected a lesser amount to position the retainer 416 within bore 462 of the bone plate 412. With reference to FIG. 17, the retainer 416 includes bone plate engaging portions 431, 433 shaped to firmly engage a bore wall 440 (see FIG. 20) of the bone plate 412, as will be discussed in greater detail below. Transverse portions 432, 434 of the retainer 416 extend inward from the bone plate engaging portions 431, 433 toward interference portions 442, 444 which each include a straight 446, 448. With reference to FIGS. 18 and 19, the retainer 416 is shown disposed above the bone anchor 418 in a throughbore 462 of the pair of non-dynamized throughbores 413. The bore wall 440 defines a groove 464 shaped to accommodate a rectangular cross-section of the retainer 416, as shown in FIG. 18. When the bone anchor 418 is driven into the bore 462 at an angle in the cephalad/caudal plane and a head 466 of the bone anchor 418 is seated within the bore 462, the retainer interference portion 442 overlaps the head 466 of the bone anchor 418 to resist back-out, as shown in FIG. 19. Further, the retainer transverse portion 432 extends radially outward toward the groove 464 and is generally out of the way of the bone anchor head 466 seated within the throughbore 462.

With respect to FIGS. 20 and 21, the bore wall 440 includes a plurality of walls sized to compliment the outer profile of the resilient retainer 416 and resist rotation of the retainer 416 during installation of the bone anchor 418. More specifically, the bore wall 440 includes an end wall 480 and opposite side walls 482, 484 separated from transverse end walls 486, 488 by corners 490, 492. With the retainer 416 disposed within the groove 464, as shown in FIG. 21, spaced ends 494, 496 of the retainer 416 extend along the end wall 480 with a complimentary curvature until reaching the straights 446, 448 at which point the retainer 416 extends away from the opposite side walls 482, 484. The retainer 416 also includes elbows 498, 500 disposed between transverse portions 432, 434 and bone plate engaging portions 431, 433 that firmly engage opposite side walls 482, 484 and resist rotation of the retainer 416 as the bone anchor 418 is rotated within the throughbore 462 in directions 502, 504, respectively.

Figure 23:
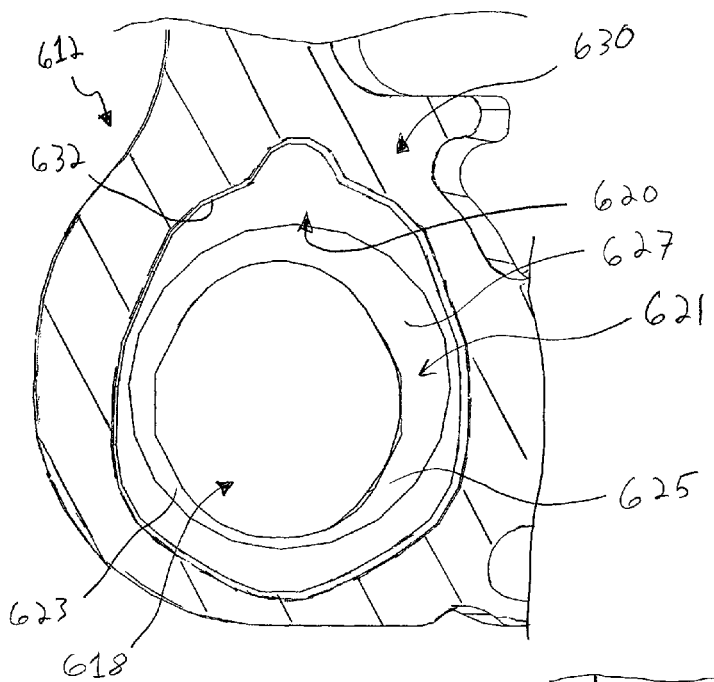
FIG. 23 is a cross-sectional view of the bone plate system of FIG. 22 taken along line 23-23 in FIG. 22 showing a throughbore with an associated retainer and bone anchor removed.
Figure 24:
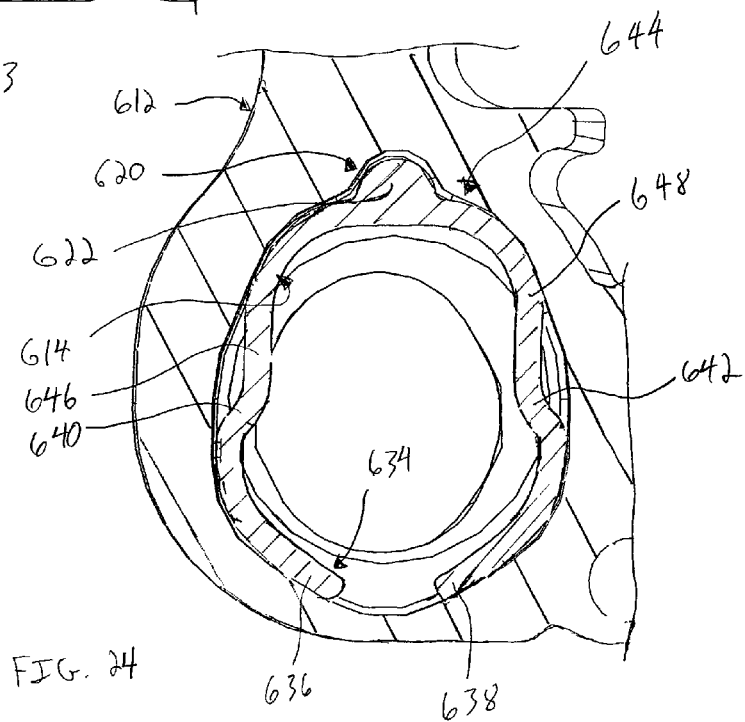
FIG. 24 is a cross-sectional view of the bone plate system of FIG. 22 similar to FIG. 23 showing the retainer positioned within the throughbore.

A bone plate system 610 in accordance with another form of the present invention is shown in FIGS. 22-26. The bone plate system 610 is similar to the bone plate systems 10, 410 and comprises a bone plate 612 having a resilient retainer 614 for resisting back-out of a bone screw 616 from a throughbore 618 of the bone plate 612. Unlike the bone plate systems 10, 410, the bone plate system 610 includes a tab recess 620 in communication with the throughbore 618 for receiving a tab 622 of the associated retainer 614. As shown in FIGS. 23 and 24, the bone plate 612 includes a bore wall 630 which defines the tab recess 620 in a transverse end wall 632 of the throughbore 618.

As shown in FIG. 23, the bone plate 612 has a spherical throughbore seat 621 extending around the throughbore 618. Unlike the seats of throughbores 60 and 462, the seat 621 has a continuous seating surface 623 extending around the entire throughbore 618. The seat 621 does, however, have a narrow portion 625 and a wide portion 627 for engaging a head 629 of the bone anchor 616.

Another difference between the bone plate system 610 and the bone plate systems 10, 410 is that the retainer 614 has a wide, open end portion 634 with a pair of spaced ends 636, 638 adjacent a pair of transverse portions 640, 642 and a narrow, closed end portion 644 adjacent a pair of interference portions 646, 648. By contrast, the narrow open end portions 150, 450 of the retainers 60, 430 are adjacent their respective interference portions 94, 95 and 442, 444.

Turning to FIGS. 25 and 26, further details of the retainer 614 are disclosed. The retainer 614 generally has a pair of arms 651, 653 with the transverse portions 640, 642 and the interference portions 646, 648 extending therealong. The arms 651, 653 generally have a uniform width 652 in the range of approximately 0.01 inches to approximately 0.03 inches, preferably approximately 0.02 inches. The retainer 614 includes bone plate engaging portions 654, 656 having a generally straight configuration extending along axes 658, 660 that are disposed at an angle γ relative to one another in the range of approximately 60° to approximately 120°, preferably approximately 90°. The transverse portions 640, 642 may have an outer radius 672 in the range of approximately 0.04 inches to approximately 0.07 inches, preferably approximately 0.055 inches, and an inner radius 670 in the range of approximately 0.02 inches to approximately 0.05 inches, preferably approximately 0.035 inches. Further, the transverse portions 640, 642 may extend at an angle 669 relative to one another, the angle 669 being in the range of approximately 60° to approximately 90°, preferably 78°.

The transverse portions 640, 642 may be separated by a distance 674 in the range of approximately 0.15 inches to approximately 0.22 inches, preferably approximately 0.185 inches. The retainer 614 may have bone plate engaging portions 676, 678 adjacent the interference portions 646, 648, the bone plate engaging portions 676, 678 having an inner radius 680 in the range of approximately 0.05 inches to approximately 0.08 inches, preferably approximately 0.065 inches. The bone plate engaging portions 676, 678 may also have an outer radius 682 in the range of approximately 0.07 inches to approximately 0.10 inches, preferably approximately 0.085 inches. The interference portions 646, 648 of the retainer 614 may have an outer width 684 in the range of approximately 0.18 inches to approximately 0.27 inches, preferably approximately 0.225 inches. Similarly, the bone plate engaging portions 654, 656 may have an outer width 686 in the range of approximately 0.21 inches to approximately 0.32 inches, preferably approximately 0.265 inches. The retainer 614 may have points 690, 692 representing the centers of the radius of curvature of the bone plate engaging portion 656 and the bone plate engaging portion 678. The retainer 614 may have a distance 688 between the points 690, 692 in the range of approximately 0.08 inches to approximately 0.13 inches, preferably approximately 0.108 inches. In another aspect, the retainer 614 has a distance 694 between ends of the bone plate engaging portions 654, 656 and an inner surface 693 of the closed end portion 644. The distance 694 may be in the range of approximately 0.23 inches to approximately 0.34 inches, preferably approximately 0.288 inches. Further, the retainer 614 may have a distance 696 between the inner surface 693 of the closed end portion 644 and an outermost point of the tab 622. The distance 696 may be in the range of approximately 0.02 inches to approximately 0.07 inches, preferably approximately 0.05 inches. With reference to FIG. 26, the retainer 614 may have a thickness 698 in the range of approximately 0.015 inches to approximately 0.025 inches, preferably approximately 0.02 inches.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bone plate system comprising:
   an elongate bone plate having a longitudinal axis;
   a throughbore of the bone plate having a predetermined axial length along the bone plate axis with the throughbore having a pair of opposite axial end portions along the axial length of the throughbore;
   a bone anchor;
   an enlarged head of the bone anchor for being received in the throughbore;
   a resilient retainer disposed in the throughbore;
   a pair of elongate arm portions of the resilient retainer extending along opposite sides of the throughbore;
   interference portions of the elongate arm portions disposed in the throughbore to be adjacent or in a predetermined one of the axial end portions of the throughbore;
   bone plate engaging portions of the resilient retainer at the other axial end portion of the throughbore with the other axial end portion of the throughbore and the bone anchor head being configured and sized relative to each other to allow the bone anchor to extend obliquely in the throughbore with a raised portion of the bone anchor head generally level with the retainer bone plate engaging portions at the other axial end portion of the throughbore and a lowered portion of the bone anchor head disposed below the retainer interference portions in the throughbore so that the retainer interference portions are in interference with the bone anchor head lowered portion to resist back-out of the bone anchor from the throughbore; and
   the retainer interference portions and bone anchor head are configured so that with the interference portions extending above the lowered portion of the bone anchor head no portion of the bone anchor head extends over the interference portions.

2. The bone plate system of claim 1 wherein the bone plate includes a throughbore seat extending about the throughbore for engaging the bone anchor head, the seat having a wide portion disposed below the interference portions and a narrow portion offset along the axial length of the throughbore from the wide portion of the throughbore seat.

3. The bone plate system of claim 2 wherein the throughbore has a central bore axis, the bone anchor includes a shank depending from the enlarged head, and the throughbore seat includes a wall extending below the narrow portion of the seat which engages the bone anchor shank and limits the bone anchor to a predetermined maximum oblique angle relative to the central bore axis.

4. The bone plate system of claim 3 wherein the bone plate has a predetermined thickness adjacent the throughbore and the enlarged head of the bone anchor has an outer diameter greater than the predetermined thickness of the bone plate and is sized such that the raised portion of the enlarged head does not extend above the bone plate with the enlarged head received in the throughbore and the bone anchor extending at the predetermined maximum oblique angle relative to the bore axis.

5. The bone plate system of claim 1 wherein the throughbore is elongated to include an intermediate portion between the axial end portions, and the interference portions are disposed in the intermediate portion of the throughbore adjacent the predetermined one axial end portion of the throughbore.

6. The bone plate system of claim 1 wherein the bone plate has a bore wall extending around the throughbore and a recess of the bore wall which opens to the throughbore, and the bone plate engaging portions of the resilient retainer are disposed in the recess at the other axial end portion of the throughbore.

7. The bone plate system of claim 1 wherein the throughbore is configured to be a non-dynamized throughbore with the interference portions in the predetermined one axial end portion of the throughbore.

8. The bone plate system of claim 7 wherein the other axial end portion of the throughbore and the bone anchor head are configured and sized relative to each other to allow the bone anchor to extend obliquely in the throughbore and an uppermost portion of the enlarged head of the bone anchor to extend above the resilient retainer.

9. The bone plate system of claim 1 wherein the bone anchor has a longitudinal axis, the enlarged head of the bone anchor includes a radially enlarged lower portion having a lower curved surface and an upper flat surface, and the upper flat surface extends generally orthogonal to the bone anchor longitudinal axis.

10. The bone plate system of claim 9 wherein the enlarged head of the bone anchor has a predetermined axial height and the curved surface of the radially enlarged lower portion has a generally spherical configuration with a radius of curvature greater than the axial height of the enlarged head.

11. The bone plate system of claim 9 wherein the upper flat surface and the lower curved surface have a radially outer corner junction therebetween, and the enlarged head includes an annular wall upstanding from the upper flat surface at a position radially inward from the outer corner junction.

12. The bone plate system of 11 wherein the outer corner junction comprises a cylindrical wall extending between the upper flat surface and the lower curved surface along the longitudinal axis of the bone anchor.

13. The bone plate system of claim 1 wherein the elongate arm portions of the resilient retainer include transition portions adjacent the interference portions, the transition portions extending obliquely to the interference portions.

14. The bone plate system of claim 13 wherein the lowered portion of the bone anchor head is disposed below the transition portions in the throughbore.

15. The bone plate system of claim 1 wherein the enlarged head of the bone anchor has an outer diameter and the interference portions of the resilient retainer each extend across the lowered portion of the enlarged head a distance that is less than half the outer diameter of the enlarged head.

16. The bone plate system of claim 1 wherein the enlarged head of the bone anchor has an outer diameter and the interference portions of the resilient retainer are spaced apart by a distance less than the outer diameter of the enlarged head.

17. The bone plate system of claim 1 wherein the bone plate has a bore wall extending about the throughbore and the interference portions of the elongate arm portions are spaced from the bore wall along the length of the interference portions.

18. The bone plate system of claim 1 wherein the bone plate includes a recess configured to receive at least the bone plate engaging portions of the resilient retainer and the bone plate further includes a throughbore seat extending about the throughbore for engaging the bone anchor head and the entirety of the throughbore seat is disposed below the recess of the bone plate.

19. The bone plate system of claim 1 wherein the bone plate includes a throughbore seat extending about the throughbore for engaging the bone anchor head, the seat having a wide portion disposed at or adjacent the one axial end portion of the throughbore and a narrow portion disposed at the other axial end portion of the throughbore.

20. The bone plate system of claim 19 wherein the throughbore has a central bore axis, the bone anchor has an axis and includes a shank depending from the enlarged head along the bone anchor axis, and the bone plate includes a wall extending below the narrow portion of the througbore seat for engaging the bone anchor shank to limit orientation of the bone anchor axis relative to the central bore axis to a predetermined maximum oblique angle therebetween.

21. The bone plate system of claim 1 wherein the resilient retainer has a generally looped configuration about the throughbore with a predetermined length about the throughbore and a transverse cross-sectional configuration that is substantially uniform along at least a majority of the length of the retainer.

22. The bone plate system of claim 21 wherein the resilient retainer includes a tab intermediate the elongate arm portions along the length of the retainer with a different transverse cross-sectional configuration than the transverse cross-sectional configuration of the elongate arm portions.

23. The bone plate system of claim 21 wherein the transverse cross-sectional configuration of the resilient retainer is substantially uniform along the entire length of the retainer.

24. The bone plate system of claim 23 wherein the interference portions and the bone plate engaging portions have substantially the same transverse cross-sectional configuration.

25. The bone plate system of claim 1 wherein the bone anchor enlarged head has a substantially annular upwardly facing surface, a lower curved surface, and a radially outer corner junction between the upwardly facing surface and the lower curved surface; and
the raised portion of the bone anchor head includes a portion of the radially outer corner junction of the bone anchor head.

26. The bone plate system of claim 1 wherein the bone anchor enlarged head includes an upwardly facing surface and a generally annular wall upstanding from the upwardly facing surface radially inward therefrom; and
the lowered portion of the bone anchor head includes a portion of the upwardly facing surface of the bone anchor head.

27. A bone plate system comprising:
a bone plate having top and bottom surfaces;
a plurality of throughbores of the bone plate each extending through the bone plate and having openings in both the top and bottom surfaces for receiving bone anchors therethrough;
bore walls extending about the throughbores;
a resilient retainer received in each of the throughbores; and
a pair of substantially parallel, straight interference portions of each of the resilient retainers disposed in an associated throughbore and extending along either side of the throughbore spaced from the bore wall thereof to be completely exposed in the throughbore and spaced from each other across the throughbore to retain a head portion of a bone anchor received therein.

28. The bone plate system of claim 27 wherein the top surface openings each include an axis extending along the bone plate, the throughbores each include opposite axial end portions, and the resilient retainers each have a generally looped configuration with opposite end portions of each of the retainers disposed at opposite axial end portions of the corresponding throughbore.

29. The bone plate system of claim 28 wherein the generally looped configuration of the resilient retainers comprises an open looped configuration such that one end portion is closed and the opposite end portion is open.

30. The bone plate system of claim 28 wherein the top surface openings have elongated, generally elliptical shapes having respective major and minor diameters, and the major diameters are aligned with the opening axes such that the opposite axial end portions of the openings are spaced apart from one another along the major axes of the top surface openings.

31. The bone plate system of claim 27 wherein the top surface openings each include an axis extending along the bone plate and a predetermined axial length, and the interference portions of the resilient retainers extend across the throughbore an axial distance less than the predetermined top surface opening axial length.

32. The bone plate system of claim 27 in combination with bone anchors having head portions with a substantially similar outer diameter and the interference portions of each resilient retainer are spaced apart by a distance less than the outer diameter of the head portion.

33. The bone plate system of claim 27 wherein each of the resilient retainers includes a pair of transverse portions oriented to extend transverse to the substantially parallel, straight interference portions and be completely exposed in the throughbore.

34. The bone plate system of claim 27 in combination with bone anchors having head portions and the bone plate and bone anchor head portions have curved engagement surfaces that are configured to engage each other with the bone anchors driven into the bone plate throughbores and permit pivoting of the bone anchor head portions in the throughbores due to the engagement of the curved engagement surfaces.

35. The bone plate system of claim 27 wherein the resilient retainers include bone plate engaging portions configured for being held in the bone plate and transition portions extending between the bone plate engaging portions and the interference portions.

36. The bone plate system of claim 35 wherein the bore walls include recesses which open to the throughbores and the bone plate engaging portions of the resilient retainers are disposed in the recesses.

37. A bone plate system comprising:
a bone plate having a throughbore including opposite axial end portions and an axis extending therebetween;
an elongate bone anchor;
a head portion of the bone anchor configured to be received in the throughbore;
a resilient retainer disposed in the throughbore configured to resist anchor back-out therefrom and having a transverse cross-sectional configuration;
a pair of interference portions of the resilient retainer that are spaced from each other and extend along either side of the throughbore between the opposite end portions of the throughbore to be completely exposed therein for the entirety of the cross-section of the interference portions and for being in interference with and overlying the bone anchor head portion;
a bore wall of the bone plate extending about the throughbore and having a recess in the bore wall which opens to the throughbore and extends outward from the opposite end portions of the throughbore; and
a pair of opposite end portions of the resilient retainer disposed outwardly from the opposite end portions of the throughbore with the opposite end portions of the resilient retainer disposed entirely in the recess outwardly from the opposite end portions of the throughbore for the entirety of the cross-section thereof so as to permit the bone anchor to be inserted into the throughbore without contacting either of the opposite end portions of the resilient retainer.

38. The bone plate system of claim 37 wherein the throughbore has a predetermined axial length along the bone plate and the interference portions of the resilient retainer extend along the throughbore an axial distance less than the predetermined axial length of the throughbore.

39. The bone plate system of claim 37 wherein the interference portions of the resilient retainer include substantially parallel straight portions.

40. The bone plate system of claim 37 wherein the resilient retainer includes transition portions extending between one of the end portions of the resilient retainer disposed in the recess and the interference portions extending along the throughbore.

41. The bone plate system of claim 37 wherein the bone anchor head portion includes a curved lower surface and the bone plate includes a seating surface disposed below the recess in the throughbore, the seating surface having a curvature complimentary to the lower surface of the bone anchor head portion.

42. The bone plate system of claim 37 wherein the interference portions of the resilient retainer have a retention position where the interference portions are positioned outside of the recess and a pass-through position where the interference portions are resiliently deflected toward the recess.

43. The bone plate system of claim 37 wherein the opposite end portions of the resilient retainer include a narrow end portion and a wide end portion.

44. The bone plate system of claim 43 wherein the wide end portion comprises a pair of straight portions extending obliquely relative to each other.

45. The bone plate system of claim 43 wherein the wide end portion comprises an open end with a pair of free ends.

46. The bone plate system of claim 37 wherein the opposite end portions of the resilient retainer include an open end and a closed end, the open end comprising a pair of free ends disposed within the recess.

47. A bone plate system comprising:
a bone plate;
a plurality of throughbores of the bone plate for receiving bone anchors;
bore walls extending about the throughbores;
a resilient retainer received in one of the throughbores;
a pair of elongate portions of the resilient retainer disposed in the one throughbore and extending in the throughbore spaced apart from each other and from the bore wall thereof to be completely exposed in the throughbore to retain a head portion of the bone anchor received therein; and
each of the resilient retainer elongate portions completely exposed in the throughbore includes a first portion and a second portion oriented to extend transversely to each other in the throughbore.

48. The bone plate system of claim 47 wherein the first portions of the resilient retainer include substantially straight portions.

49. The bone plate system of claim 48 wherein the straight portions of the resilient retainer are oriented to extend substantially parallel to one another.

50. The bone plate system of claim 47 wherein at least one of the resilient retainer elongate portions includes a curved portion bending inwardly into the throughbore and the curved portion includes the first portion and the second portion thereon.

51. The bone plate system of claim 47 wherein the bore wall of the one throughbore includes a recess extending outwardly from the throughbore and the resilient retainer includes spaced, free ends secured in the recess.

52. The bone plate system of claim 47 wherein the one throughbore includes a bore central axis and a predetermined maximum distance across the throughbore generally perpendicular to the bore central axis; and
the elongate portions of the resilient retainer extend across the associated throughbore a distance less than the predetermined maximum distance across the throughbore.

53. The bone plate system of claim 47 wherein the one throughbore includes end portions on opposite sides of the throughbore and the bore wall of the throughbore includes a recess extending outwardly from the throughbore end portions; and
the retainer received in the throughbore has a transverse cross-sectional configuration and a pair of opposite end portions disposed entirely in the recess outwardly from the opposite end portions of the throughbore for the entirety of the cross-section thereof so as to permit the bone anchor to be inserted into the throughbore without contacting either of the opposite end portions of the resilient retainer.

54. The bone plate system of claim 47 in combination with a bone anchor having a head portion and the bone plate and bone anchor head portion have curved engagement surfaces that are configured to engage each other with the bone anchor driven into the one bone plate throughbore and permit pivoting of the bone anchor head portion in the throughbore due to the engagement of the curved engagement surfaces.

55. A bone plate system comprising:
a bone plate;
a plurality of throughbores of the bone plate;
a plurality of bone anchors for extending through respective throughbores;

one of the bone anchors having a head portion, a shank portion depending from the head portion, and a longitudinal axis extending between the head portion and the shank portion;

rotary drive structure of the bone anchor head portion;

a substantially annular upwardly facing surface of the bone anchor head portion extending about and laterally outward from the rotary drive structure;

the bone anchor head portion having no portion thereof that extends laterally over the annular upwardly facing surface;

a resilient retainer in one of the throughbores;

an elongate body of the resilient retainer extending about the one throughbore;

an intermediate curved portion of the retainer body having a predetermined curvature; and curved retention portions of the retainer body with the intermediate curved portion between the curved retention portions along the retainer body and having different curvatures than the curvature of the intermediate curved portion, the curved retention portions of the retainer body being configured to shift apart to permit the head portion of the one bone anchor to be advanced into the one throughbore and shift back toward each other above the annular upwardly facing surface of the bone anchor head portion to inhibit back out of the one bone anchor from the one throughbore.

56. The bone plate system of claim 55 wherein the one throughbore includes a bore central axis extending therethrough and the curved retention portions of the retainer body each have a radius of curvature centered on a point eccentric to the bore central axis.

57. The bone plate system of claim 55 wherein the curved retention portions of the retainer body have more gradual curvatures than the curvature of the intermediate curved portion.

58. The bone plate system of claim 55 wherein the intermediate curved portion of the retainer body includes a pair of curved portions with curvatures different from each other and the curvatures of the curved retention portions of the retainer body.

59. The bone plate system of claim 55 wherein the retainer body includes a straight portion between one of the curved retention portions and the intermediate curved portion along the retainer body.

60. The bone plate system of claim 55 wherein the retainer body includes a pair of straight portions between the curved retention portions and the intermediate curved portion along the retainer body.

61. The bone plate system of claim 55 wherein the curved retention portions of the retainer body have the same curvature.

62. The bone plate system of claim 55 wherein the bone plate includes a bore wall extending about the one throughbore and a recess in the bore wall extending outwardly from the throughbore; and the intermediate curved portion of the retainer body being secured to the bone plate in the bore wall recess.

63. The bone plate system of claim 55 wherein the bone plate includes a bore wall extending about the one throughbore and a recess in the bore wall extending outwardly from the throughbore; and the elongate body of the resilient retainer has a cross-sectional configuration transverse to the length thereof and the intermediate curved portion is disposed entirely in the recess outwardly from the throughbore for the entirety of the cross-section of the intermediate curved portion.

64. The bone plate system of claim 55 wherein the one throughbore has opposite end portions and the bone plate has a bore wall extending about the one throughbore;

a recess in the bore wall extending outwardly from the throughbore opposite end portions; and the elongate body of the resilient retainer has a cross-sectional configuration transverse to the length thereof and a pair of opposite end portions disposed entirely in the recess outwardly from the opposite end portions of the throughbore for the entirety of the cross-section of the retainer end portions so as to permit the bone anchor to be inserted into the throughbore without contacting either of the opposite end portions of the resilient retainer.

65. The bone plate system of claim 64 wherein one of the opposite end portions of the retainer body includes the intermediate curved portion.

66. The bone plate system of claim 55 wherein the bone anchor head portion includes a curved lower surface and a radially outer corner junction between the annular upwardly facing surface and the lower curved surface.

67. The bone plate system of claim 55 wherein the annular upwardly facing surface of the one bone anchor head portion is substantially flat.

68. The bone plate system of claim 55 wherein the bone plate includes a bore wall extending about the one throughbore and the curved retention portions of the retainer body are spaced from the bore wall to be completely exposed in the throughbore.

69. The bone plate system of claim 55 wherein the curved retention portions of the retainer body extend along opposite sides of the one throughbore.

70. The bone plate system of claim 55 wherein the elongate body of the resilient retainer has a generally looped configuration about the throughbore including a pair of end portions on opposite sides of the throughbore with one end portion being closed and the other end portion being open.

71. The bone plate system of claim 55 wherein the bone plate includes a bore wall extending about the one throughbore and a recess in the bore wall that opens to the throughbore and the retainer includes a pair of free ends disposed in the recess.

72. The bone plate system of claim 55 wherein the curved retention portions both have one of a concave curvature and a convex curvature and the retainer body includes curved portions adjacent the curved retention portions along the retainer body having the other of the concave curvature and the convex curvature.

* * * * *